(12) United States Patent
Agata et al.

(10) Patent No.: US 6,900,239 B2
(45) Date of Patent: May 31, 2005

(54) TUMOR CHEMOPOTENTIATION USING ISOCOUMARIN DERIVATIVES

(75) Inventors: Naoki Agata, Brookline, MA (US); Surender Kharbanda, Natick, MA (US)

(73) Assignee: ILWZ ILEX Products, Inc., San Antonio, TX (US)

( * ) Notice: Subject to any disclaimer, the term of this patent is extended or adjusted under 35 U.S.C. 154(b) by 0 days.

(21) Appl. No.: 10/082,521

(22) Filed: Feb. 23, 2002

(65) Prior Publication Data

US 2002/0165210 A1 Nov. 7, 2002

Related U.S. Application Data

(63) Continuation-in-part of application No. 09/794,417, filed on Feb. 27, 2001, now Pat. No. 6,589,981.
(60) Provisional application No. 60/186,071, filed on Feb. 29, 2000, now abandoned.

(51) Int. Cl.$^7$ .............................................. A61K 31/35
(52) U.S. Cl. ........................... 514/456; 514/33; 514/89; 514/177; 514/178; 549/289; 424/649
(58) Field of Search ........................... 514/456, 89, 33, 514/177, 178, 90, 34; 424/649; 549/289

(56) References Cited

U.S. PATENT DOCUMENTS 6,020,363 A * 2/2000 Hirano et al. ............... 514/456

OTHER PUBLICATIONS

Stein, J. H., Editor–in–Chief, Internal Medicine, Fourth Edition, Chapters 71 and 72, 1994.*
DiPiro, J. T., Editor–in–Chief, Pharmacotherapy, A Pathophysiologic Approach, pp. 1354, 1355, and p. 1496, 1989.*
Teicher et al., "Optimal Scheduling of Interleukin–12 and Fractionated Radiation Therapy in the Murine Lewis Lung Carcinoma," Radiation Oncology Investigations, 6:71–80, 1998.
Kawai et al., Enhancement of Anticancer Effects of Radiation and Conventional Anticancer Agents by a Quniolinone derivative, Vesnarinone: Studies on Human Gastric Cancer Tissues in Nude Mice, Anticancer Res., 18:405–412, 1998.
Voest et al., "Inhibition of Angiogenesis In Vivo by Interleukin 12," J. Nat'l Cancer Inst., 87:581–586, 1995.
Gorski et al., Blockade of the Vascular Endothelial Growth Factor Stress Response Increases the Antitumor Effects of Ionizing Radiation, Cancer Res., 59:3374–3378, 1999.
Norioka et al., Interaction of Interleukin–1 and Interferon–g on Fibroblast Growth Factor–Induced Angiogenesis, Jpn. J. cancer Res., 85:522–529, 1994.
Mauceri et al., "Combined effects of Angiostatin and Ionizing Radiation in Antitumor Therapy," Nature, 394:287–291, 1998.
Matsumoto et al. "Synthesis and Biological Evaluation of Cytogenin Derivatives," J. Antibiotics, 54:285–296, 2001.
Salloum et al., NM–3, an Isocoumarin, Increases the Antitumor Effect of radiotherapy without Toxicity, Cancer Res., 60:6958–6963, 2000.
Agata et al., NM–3, a Novel Angiogenesis Inhibitor, Potentiates Dexamethasone–Induced Apoptosis in Multiple Myeloma Cells, Proceedings of the 2001 AACR–NCI–EORTC International Conference, p67 Oct. 2001.
Yin et al., "The Novel Isocoumarin 2–(8–Hydroxy–6–methoxy–1–oxo–1H–2–benzopyran–3–yl) Propionic Acid (NM–3) Induces lethality of Human Carcinoma Cells by Generation of Reactive Oxygen Species," Mol. cancer Therapeutics, 1:43–48, 2001.
Reimer et al., "Antineoplastic Effects of Chemotherapeutic Agents are Potentiated by NM–3, an Inhibitor of Angiogenesis," Cancer Res., 62:789–795, 2002.
Nakashima, et al., "Inhibition of Angiogenesis by a New Isocoumarin NM–3," J. Antibiotics, 52:426–428, 1999.
Kumagi, et al., "Antitumor Activity of Cytogenin," J. Antibiotics, 48:175–178, 1995.
Oikawa, et al., "Effects of Cytogenin, a Novel Microbial Product, on Embryonic and Tumor Cell–Induced Angiogenic Responses In Vivo," Anticancer Res., 17:1881–1889, 1997.

* cited by examiner

Primary Examiner—Dwayne Jones
(74) Attorney, Agent, or Firm—Stephen J. Moloney; Al A. Jecminek

(57) ABSTRACT

A method for enhancing the efficacy of chemotherapy in the treatment of cancer in animals, particularly humans, is provided wherein isocoumarin derivatives that exhibit unique chemopotentiation properties are employed in a combination treatment with chemotherapy.

18 Claims, 14 Drawing Sheets

Effect of NM-3 and paclitaxel on 50mm³ pre-existing MDAMB435 tumor xenografts.

Effect of NM-3 and paclitaxel on 100 mm³ pre-existing MDAMB-435 tumor xenografts.

Comparison of NM-3 dosing regimes against 100 mm³ pre-existing MDAMB435 tumor xenografts: daily, bid, and continuous.

Effects of 5-FU/NM-3 on MDAMB-435 human breast tumor xenografts

Effect of NM-3, IR and the Combination on Lewis Lung Carcinoma tumors

Effect of NM-3, IR and the Combination on the Growth of Seq-1 Tumors in Nude Mice

TUMOR CHEMOPOTENTIATION USING ISOCOUMARIN DERIVATIVES

This application is a continuation-in-part of U.S. application Ser. No. 09/794,417, filed Feb. 27, 2001, now U.S. Pat. No. 6,589,981, which claims priority to Provisional Application Ser. No. 60/186,071, filed Feb. 29, 2000 now abandoned.

BACKGROUND OF THE INVENTION

1. Field of the Invention

This invention relates to isocoumarin derivatives and their use in cancer therapy. More particularly, it relates to the use of isocoumarin derivatives in the prevention or treatment of cancer by inhibiting tumor neovascularization, or angiogenesis, in combination with enhancing tumor sensitivity to radiation therapy and/or chemotherapy.

2. Description of Related Art

Normal tissue homeostasis is achieved by an intricate balance between the rate of cell proliferation and cell death. Disruption of this balance either by increasing the rate of cell proliferation or decreasing the rate of cell death can result in the abnormal growth of cells and is thought to be a major event in the development of cancer. The effects of cancer are catastrophic, causing over half a million deaths per year in the United States alone. Conventional strategies for the treatment of cancer include chemotherapy, radiotherapy, surgery, biological therapy or combinations thereof. However, further advances in these strategies are limited by lack of specificity and excessive toxicity to normal tissues. In addition, certain cancers are refractory to treatments such as chemotherapy, and some of these strategies, such as surgery, are not always viable alternatives.

Once the diagnosis of cancer is established, the most urgent question is whether the disease is localized or has spread to lymph nodes and distant organs. The most fearsome aspect of cancer is metastasis, and this fear is well justified. In nearly 50% of patients, surgical excision of primary neoplasms is ineffective, because metastasis has occurred by the time the tumor is large enough for resection (Sugarbaker, 1979; Fidler & Balch, 1987). Metastases can be located in different organs and in different regions of the same organ, making complete eradication by surgery, radiation, drugs or biotherapy difficult. Furthermore, the organ microenvironment significantly influences the response of tumor cells to therapy (Fidler, 1985), as well as the efficiency of anticancer drugs, which must be delivered to tumor foci in amounts sufficient to destroy cells without causing undesirable side effects (Fidler & Poste, 1985). In addition, the treatment of metastatic cancer is greatly hindered due to the biological heterogeneity of cancer cells, and the rapid emergence of tumor cells that become resistant to most conventional anticancer agents (Fidler & Poste, 1985).

One of the processes involved in the growth of both primary and secondary (metastatic) tumors is neovascularization, or creation of new blood vessels which grow into the tumor. This neovascularization is termed angiogenesis (Folkman, 1986; Folkman, 1989), which provides the growing tumor with a blood supply and essential nutrients. Although tumors of 1–2 mm in diameter can receive all nutrients by diffusion, further growth depends on the development of an adequate blood supply through angiogenesis. Inhibition of angiogenesis provides a novel and more general approach for treating metastases by manipulation of the host environment.

Several angiogenic molecules released by both tumor endothelial cells and the normal cells surrounding the tumor endothelial cells mediate the induction of angiogenesis. The prevascular stage of a tumor is associated with local benign tumors, whereas the vascular stage is associated with tumors capable of metastasizing. Moreover, studies using light microscopy and immunohistochemistry concluded that the number and density of microvessels in different human cancers directly correlate with their potential to invade and produce metastasis (Weidner, et al., 1991; Weidner, et al., 1993). Not all angiogenic tumors produce metastases, but the inhibition of angiogenesis prevents the growth of tumor endothelial cells at both the primary and secondary sites and thus can prevent the emergence of metastases.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent and unregulated angiogenesis is characteristic of tumor growth and it supports the pathological damage seen in cancer. Thus, tumor growth is an angiogenesis-dependent process (Folkman, 1971). After an initial prevascular phase, every increase in tumor endothelial cell population is preceded by an increase in new capillaries converging on the tumor. Expansion of tumor volume beyond this phase requires the induction of new capillary blood vessels.

Blockade of the angiogenic process has emerged as an important anticancer strategy. It has been demonstrated that in mice bearing subcutaneous Lewis lung carcinomas (3LL), the primary or local tumor releases an angiogenesis-inhibiting substance, named angiostatin (O'Reilly, et al., 1994). Angiostatin is a 38-kDa fragment of plasminogen that selectively inhibits proliferation of endothelial cells. Angiostatin has been shown to suppress vascularization and, hence, growth of metastases when used as an adjuvant to conventional therapy (e.g. see, U.S. Pat. No. 5,733,876). Several studies have produced results consistent with this model. After systemic administration, purified angiostatin can produce apoptosis in metastases (Holmgren, et al., 1995) and sustain dormancy of several human tumors implanted subcutaneously in nude mice (O'Reilly et al., 1996).

Clearly, angiogenesis plays a major role in tumor development and maintenance. As stated earlier, conventional cancer therapeutic regimens are hampered by the ability of the cancer cell to adapt and become resistant to the therapeutic modality used to combat tumor growth. Certain isocoumarin derivatives are known to have an inhibiting effect on vascularization (e.g. see, U.S. Pat. No. 6,020,363 which is incorporated herein by reference), and it is likely that such isocoumarin derivatives will be useful in reducing the growth, size, spreading, and otherwise mitigating the deleterious effect of a tumor by virtue of their angiogenesis-inhibiting properties. Significantly, pursuant to the present invention, isocoumarin derivative treatment has also been shown to sensitize endothelial cells and established tumors to the cytotoxic effects of ionizing radiation and/or conventional chemotherapy. Thus, the combination of these properties of isocoumarin derivatives provides for a promising cancer therapeutic strategy and establishes a novel medical application for these drugs.

An isocoumarin derivative, particularly 3-hydroxymethyl-6-methoxy-8-hydroxy-1H-2-benzopyran-1-one, subsequently named cytogenin (formula I, below), was first identified as a compound produced by the M143-37F11 strain of *Streptoverticillium eurocidicum*. Cytogenin has attracted attention under the name of the antibiotic M143-37F11 because of its growth-inhibiting activity against various animal cells and human cancer cells (Japanese Patent Laid-Open No. 2177/'91). Cytogenin given by oral administration demonstrated antitumor activities against several transplantable mouse solid tumors. However, this compound showed very low anti-proliferation inhibitory activity against cultured tumor cells and low toxicity in mice and dogs. The mechanism of action of antitumor activity of cytogenin was found to be associated with its ability to disrupt the neovascularization in growing tumors. While cytogenin demonstrated promise as an antitumor agent, its in vivo instability rendered it unfit for clinical development. Investigations of chemical derivatives of cytogenin identified a highly stable analog, herein referred to as NM-3 (formula II, below) that retained the important biological properties of the parent compound. NM-3 is the most extensively studied member of this class of compounds (e.g. see, U.S. Pat. No. 6,020,363), and will serve as the primary example of an isocoumarin derivative useful in the treatment methods of the present invention.

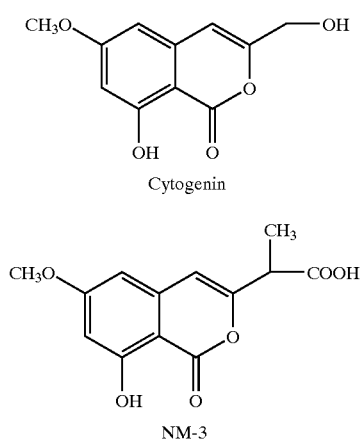

SUMMARY OF INVENTION

In its broadest aspects, the present invention is directed to the use of isocoumarin derivatives of formula III, below, in combination with ionizing radiation and/or chemotherapeutic agents in the treatment of cancer to provide a therapeutic effect, in terms of reduced cancer mass or metastatic potential, which is enhanced over that obtained with radiation and/or the chemotherapeutic agent alone.

The isocoumarin derivatives useful in the methods of the invention include compounds of formula III:

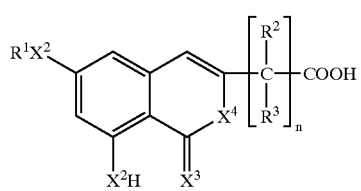

wherein each of $X^1$, $X^2$, and $X^3$ may independently be sulphur or oxygen; and $X^4$ is sulfur, oxygen or —NH—; $R^1$ is hydrogen or $C_{1-6}$ alkyl, and $R^2$ and $R^3$ may be the same or different and each represents $C_{1-6}$ alkyl, $C_{7-10}$ alkaryl, hydroxy or hydrogen, and n is zero or a whole integer of from 1 to 3. The isocoumarin derivatives of the formula III function as radiation sensitizers and/or chemopotentiators, providing therapeutic benefit in the treatment of cancer which is additive or synergistic over that obtained with the isocoumarin derivative on the one hand, or ionizing radiation on the chemotherapeutic agent on the other hand, when either is used as the single treatment modality.

Accordingly, the present invention provides a method of inhibiting the growth of a tumor cell comprising contacting said tumor cell with an isocoumarin derivative of formula III, above, and a second growth inhibiting modality (or mode of treatment) selected from a dose of ionizing radiation or a chemotherapeutic agent or combination of said radiation and chemotherapeutic agent, wherein the does of said isocoumarin derivative, when combined with the second growth inhibiting modality, is effective to inhibit growth of said tumor cell.

In one embodiment, the invention further provides a method of treating cancer in a human patient comprising administering an isocoumarin derivative of formula III, above, to a human patient together with a dose of ionizing radiation and/or a chemotherapeutic agent, wherein the dose of said isocoumarin derivative, when combined with the dose of ionizing radiation and/or chemotherapeutic agent, is effective to treat the cancer. In this embodiment the cancer subject to treatment is suitably selected from the group consisting of skin cancer, prostate cancer, lung cancer, brain cancer, breast cancer, ovarian cancer, cervical cancer, liver cancer, pancreatic cancer, colon cancer, stomach cancer, lymphoma and leukemia. In the method of the invention, the isocoumarin derivatives are suitably administered prior to, or simultaneously with, the ionizing radiation and/or chemotherapeutic agent. The invention further provides a method of potentiating the effect of ionizing radiation on a tumor cell comprising contacting the tumor cell with an isocoumarin derivative of formula III, above, and then contacting the tumor cell with ionizing radiation, as well as a method of sensitizing a tumor cell to the growth inhibiting or cell killing effects of a chemotherapeutic agent, comprising contacting the tumor cell with an isocoumarin derivative of formula III, above, and then contacting the tumor cell with the chemotherapeutic agent.

One aspect of the invention provides for the potentiation of the action of glucocorticoids on cancer cells by an isocoumarin derivative of the present invention, wherein such potentiation comprises the direct action of the isocoumarin derivative on cancer cell as compared to indirect action by inhibition of angiogenesis. Embodiments include methods for potentiating both glucocorticoid-induced cell death and glucocorticoid-induced inhibition of proliferation of cancer cells, wherein such cancer cells are contacted by both an isocoumarin derivative and a glucocorticoid, either sequentially or in combination. In some embodiments, the cell death results from apoptosis. In certain embodiments, the cancer cell is a myeloma cell, the glucocorticoid is Dexamethasone or Prednisone, and the isocoumarin derivative is NM-3. The methods also provide for further contacting the cancer cell with one or more other chemotherapeutic agents, suitable agents including Vincristine, Doxorubicin, Cyclophosphamide, Etopside, Cisplatin, Melphalan, Mitoxantrone, BCNU, Idarubicin, Procarbazine, and Cytoxan.

Other embodiments of the invention comprise methods for treating multiple myeloma in a human patient. One method comprises administering an isocoumarin derivative and a glucocorticoid to a patient. Another method provides for the administration of an isocoumarin derivative, a glucocorticoid and one or more other chemotherapeutic agents to a patient. Suitable glucocorticoids include Dexamethasone and Prednisone, and suitable isocoumarin derivatives include NM-3. When the glucocorticoid is Dexamethasone, regimens of other chemotherapeutic agents include administration of Vincristine as a third treatment modality and Doxorubicin as a fourth treatment modality. Other embodiments provide wherein the glucocorticoid is Dexamethasone and the chemotherapeutic agent(s) is/are selected from the group consisting of Vincristine, Doxorubicin, Cyclophosphamide, Etopside, Cisplatin, Melphalan, BCNU, and Idarubicin. In embodiments wherein the glucocorticoid is Prednisone, regimens of other chemotherapeutic agents administered include: the administration of Melphalan as a third treatment modality; the administration of Cyclophosphamide as a third treatment modality; and the administration of Vincristine as a third treatment modality, BCNU as a fourth treatment modality, Melphalan as a fifth treatment modality and Cyclophosphamide as a sixth treatment modality. Other embodiments provide wherein the glucocorticoid is prednisone and wherein the one or more chemotherapeutic agents is or are selected from the group consisting of Melphalan, Mitoxantrone, Cyclophosphamide, Vincristine, Procarbazine, Cytoxan, BCNU and Doxorubicin.

Further, as used herein, chemotherapeutic agent includes all conventional cytotoxic and cytostatic agents used in cancer treatment and prevention including, from a mechanism of action standpoint; Tubulin interactive agents, DNA-interactive agents, antimetabolites and antifolates, antihormonals, antibiotics, antivirals, ODC inhibitors, and other cytotoxic agents, and prodrugs.

BRIEF DESCRIPTION OF THE DRAWINGS

FIG. 11(A) shows the distribution of annexin V-FITC stained cells. FIG. 11(B) shows the dual staining for annexin V-FITC and PI.

DETAILED DESCRIPTION OF INVENTION

Figure 1:
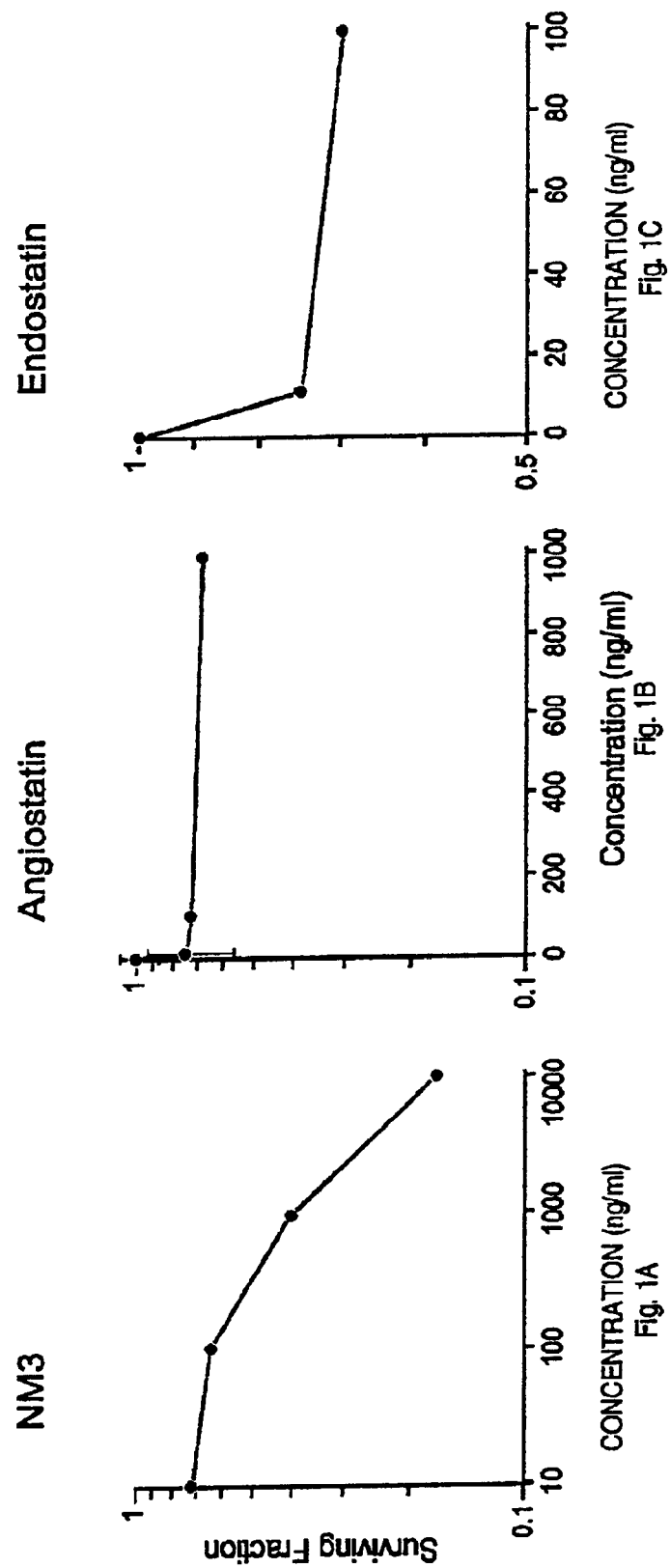
FIG. 1 is a series of three graphs showing the effects of a constant amount of gamma radiation combined with various concentrations of NM-3, angiostatin and endostatin on the number of human umbilical vein endothelial cell (HUVEC) colonies formed following treatment.

The present invention provides methods of enhancing the efficacy of conventional chemotherapy and/or radiation in the treatment of cancer in animals, particularly humans harboring such cancer, through the use of a class of isocoumarin derivatives, which exhibit unique radiosensitization activity and/or chemopotentiation properties when employed in combination with chemotherapeutic agents and/or radiation. Using the isocoumarin derivatives of the present invention in combination with conventional chemotherapy and/or radiation is anticipated to facilitate not only greater efficacy in the tumor cell killing and growth inhibition effects of the treatment, but also to afford treatment regimes which present less toxicity and/or adverse side effects to the treatment subjects, since the dosage and/or intensity of the treatment can be reduced as a result of the treatment enhancing effects of the isocoumarin derivatives.

A. Isocoumarin Derivatives

The isocoumarin derivatives of formula III, above, which are useful in the invention preferably include those wherein $X^1$, $X^2$ and $X^3$ are oxygen; $X^4$ is oxygen or sulfur; $R^1$ is $C_{1-3}$ alkyl; $R^2$ and $R^3$ are hydrogen or $C_{1-6}$ alkyl and n is 0, 1 or 2, or a pharmaceutically acceptable salt thereof. Suitable isocoumarin and thiaisocoumarin derivatives in this preferred embodiment include:

2-(8-hydroxy-6-methoxy-1-oxo-1H-2-benzopyran-3-yl) acetic acid 2-(8-hydroxy-6-ethoxy-1-oxo-1H-2-benzopyran-3-yl) propionic acid 2-(8-hydroxy-6-methoxy-1-oxo-1H-2-benzothiopyran-3-yl) acetic acid 2-(8-hydroxy-6-ethoxy-1-oxo-1H-2-benzothiopyran-3-yl) acetic acid 2-(8-hydroxy-6-methoxy-1-oxo-1H-2-benzopyran-3-yl) propionic acid 2-(8-hydroxy-6-methoxy-1-oxo-1H-2-benzothiopyran-3-yl) propionic acid In a more preferred embodiment, the isocoumarin derivatives employed in the methods of the invention have a chemical structure in accordance with formula IV, below.

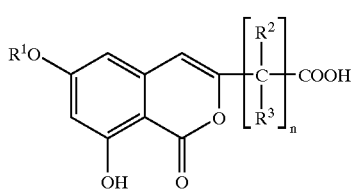

(IV)

Wherein $R^1$ is $C_{1-3}$ alkyl, and $R^2$ and $R^3$ may be the same or different and each represents a hydrogen atom or $C_{1-6}$ alkyl and n is 0 or 1. Most preferably, $R^1$ is methyl, $R^2$ is hydrogen and $R^3$ is methyl with n being the whole integer 1. This most preferred isocoumarin is set forth in formula II, above, and is hereinafter referred to as NM-3.

The isocoumarin derivatives which are useful in the methods of the present invention, may be prepared from conventional starting materials using a variety of synthetic methods described in the prior art, including the synthesis methods set forth in U.S. Pat. Nos. 6,020,363; 4,018,891; 3,975,535; 3,960,892; German Patent No. DE2448387; publications Couture, et al., 1990; Kennedy et al., 1987; Bringmann et al., 1994; Bringmann et al., 1997; Letcher et al., 1998; Dijksman & Newbold, 1951; Kiang & Mann, 1951; Woodroofe et al., 2000; Padwa et al., 1999; Norisuke, 1985; Spassov et al., 1985; Hata & Atsushi, 1983; Yousif et al., 1982; Singh et al., 1983; and Sakamoto et al., 1985, all of which are incorporated herein by reference. The techniques set forth in U.S. Pat. No. 6,020,363 are particularly useful in its synthesis of the preferred isocoumarin in accordance with this invention, including NM-3, whereas the synthetic methodology set forth in U.S. Pat. No. 3,975,535 is useful for the broader class of isocoumarin derivatives employed in the invention, including the thiaisocoumarin analogs.

The isocoumarin derivatives employed in the methods of the invention can be formulated in a variety of conventional pharmaceutical formulations and administered to cancer patients, in need of treatment, by any one of the drug administration routes conventionally employed including oral, intravenous, intraarterial, parental or intrapenitoneal. In this invention, the preferred routes of administration include intravenous (IV), intraperitoneal (IP) and oral, with oral administration being most preferred, to take advantage of the high level of oral bioavailability exhibited by NM-3 and other isocoumarin derivatives according to the invention.

For oral administration the isocoumarin derivatives of the invention may be formulated, for example, with an inert dilutent or with an assimiable edible carrier, or enclosed in hard or soft shell gelatin capsules, or compressed into tablets, or incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, a gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit for is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent methyl and propylparabens as preservatives, a dye and flavoring, such as cherry or orange flavor. Of course, any material used in preparing a dosage unit form should be pharmaceutically pure and substantially non-toxic in the amounts employed. In addition, other chemotherapeutic compounds may be incorporated into sustained-release preparation and formulations.

Pharmaceutical formulations of the isocoumarin derivatives in accordance with the invention which are suitable for injectable use include sterile aqueous solutions or dispersions and sterile powders for the extemporaneous preparation of sterile injectable solutions or dispersions. In all cases the form must be sterile and must be fluid to the extent that each syringability exists. It must be stable under the conditions of manufacture and storage and must be preserved against the contaminating action of microorganisms, such as bacteria and fungi. The carrier can be a solvent or dispersion medium containing, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active isocoumarin compounds in the required amount in the appropriate solvent with various of the other to ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the composition.

B. Chemotherapeutic Agents

The chemotherapeutic agents useful in the methods of the invention include the full spectrum of compositions and compounds which are known to be active in killing and/or inhibiting the growth of cancer cells. The chemotherapeutic agents, grouped by mechanism of action include DNA-interactive agents, antimetabolites, Tubulin interactive agents, anti-hormonals, anti-virals, ODC inhibitors and other cytotoxics such as hydroxy-urea. Any of these agents are suitable for use in the methods of the present invention.

DNA-interactive agents include the alkylating agents, e.g., Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plicamycin.

The alkylating agents form covalent chemical adducts with cellular DNA, RNA and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include: nitrogen mustards, such as Chlorambucil, Cyclophosphamide, Isofamide, Mechlorethamine, Melphalan, Uracil Mustard; aziridine such as Thiotepa; methanesulphonate esters such as Busulfan; nitroso ureas, such as Carmustine, Lomustine, Streptozocin; platinum complexes such as Cisplatin, Carboplatin; bioreductive alkylators, such as Mitomycin and Procarbazine, Dacarbazine and Altretemine; DNA strand-breaking agents including Bleomycin. Topoisomerases are ubiquitous cellular enzymes which initiate transient DNA strand breaks during replication to allow for free rotation of the strands. The functionality of these enzymes is critical to the replication process of DNA. Without them, the torsional strain in the DNA helix prohibits free rotation, the DNA strands are unable to separate properly, and the cell eventually dies without dividing. Topo I links to the 3'-terminus of a DNA single strand break, while Topo II links to the 5'-terminus of a double strand DNA break. DNA topoisomerase II inhibitors include the following: intercalators such as Amsacrine, Dactinomycin, Daunorubicin, Doxorubicin, Idarubicin and Mitoxantrone; nonintercalators such as Etoposide and Teniposide; camtothecins including Irinotecam (CDT-II) and Topotecan. A representative DNA minor groove binder is Plicamycin.

The antimetabolites generally exert cytotoxic activity by interfering with the production of nucleic acids by one or the other of two major mechanisms. Some of the drugs inhibit production of the deoxyribonucleoside triphosphates that are the immediate precursours of DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include: folate antagonists such as Methotrexate and Trimetrexate; pyrimidine antagonists such as Fluorouracil, Fluorodeoxyuridine, Azacitidine, Cytarabine, and Floxuridine; purine antagonists include Mercaptopurine, 6-thioguanine, Fludarabine, Pentostatin; sugar modified analogs include Cytarabine, Fludarabine; ribonucleotide reductase inhibitors include Hydroxyurea.

Tubulin interactive agents interfere with cell division by binding to specific sites on Tubulin, a protein that polymerizes to form cellular microtubules. Microtubules are critical cell structure units. When the interactive agents bind on the protein, the cell cannot properly form microtubules. Tubulin interactive agents include Vincristine and Vinblastine, both alkaloids and the Taxanes (Paclitaxel and Docetaxel).

Although their mechanisms of action are different, both taxanes and Vinca Alkaloids exert their biological effects on the cell microtubules. Taxanes act to promote the polymerization of Tubulin, a protein subunit of spindle microtubles. The end result is the inhibition of depolymerization of the microtubules, which causes the formation of stable and non-functional microtubles. This disrupts the dynamic equilibrium within the microtuble system, and arrests the cell cycle in the late $G_2$ and M phases, which inhibits cell replication.

Like taxanes, Vinca Alkaloids also act to affect the microtuble system within the cells. In contrast to taxanes, Vinca Alkaloids bind to Tubulin and inhibit or prevent the polymerization of Tubulin subunits into microtubules. Vinca Alkaloids also induce the depolymerization of microtubules, which inhibits microtuble assembly and mediates cellular metaphase arrest. Vinca alkaloids also exert effects on nucleic acid and protein synthesis; amino acid, cyclic AMP, and glutathione synthesis; cellular respiration; and exert immunosuppressive activity at higher concentrations.

Antihormonal agents exert cytotoxic activity by blocking hormone action at the end-receptor organ. Several different types of neoplasm require hormonal stimulation to propagate cell reproduction. The antihormonal agents, by blocking hormone action, deprive the neoplastic cells of a necessary stimulus to reproduce. As the cells reach the end of their life cycle, they die normally, without dividing and producing additional malignant cells. Antihormonal agents are typically derived from natural sources and include: Estrogens, Conjugated Estrogens and Ethinyl Estradiol and Diethylstibesterol, Chlortrianisen and Idenestrol; progestins such as Hydroxyprogesterone Caproate, Medroxyprogesterone, and Megestrol; androgens such as Testosterone, Testosterone Propionate; Fluoxymesterone, Methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. This group includes the glucocorticoid compounds Prednisone, Dexamethasone, Methylprednisolone, and Prednisolone. Glucocorticoids also have antiproliferative activity and promote apoptosis in eosinophils and normal and neoblastic lymphoid cells. This has led to the use of glucocorticoids in the therapy of malignant lymphoproliferative disorders and several solid tumors (Coleman, 1992; Gaynon & Lustig, 1995; Pirotte et al., 1997). Compelling evidence indicates that glucocorticoids as a group exert their antiproliferative and apoptotic effects on cells sensitive to such action via a common mechanism, i.e., binding to the glucocorticoid receptor that results in DNA binding and transcriptional regulation of specific genes (Geley et al, 1996; Ramdas et al., 1999; Planey & Litwack, 2000; Tonko et al., 2001). Glucocorticoids are used extensively in the treatment of multiple myeloma. For example, Dexamethasone is used either as a single agent (Alexanian et al., 1992, herein incorporated by reference) or in combination regimens such as "VAD," i.e., Vincristine, Doxorubicin (Adriamycin) and Dexamethasone (Barlogie et al., 1984; Segeren et al., 1999, both herein incorporated by reference) and other regimens including agents such as Cyclophosphamide, Etopside, Cisplatin, Melphalan, BCNU, Thalidomide and Idarubicin (Anderson et al., 2000; Gahrton & Durie, 1996, both herein incorporated by reference). Prednisone is also extensively used in a number of different regimens including: Prednisone and Melphalan (Gregory et al., 1992; Myeloma Trialists' Collaborative Group, 1998, both herein incorporated by reference); Prednisone and Cyclophosphamide (Bergsagel, 1998, herein incorporated by reference); and Prednisone, Vincristine, BCNU, Melphalan and Cyclophosphamide (Gregory, et al., 1992; Case et al., 1977, both herein incorporated by reference). Other agents used in Prednisone combinations regimens include Procarbazine, Cytoxan, Mitoxantrone and Doxorubcin (Adriamycin) (Anderson et al., 2000; Gahrton & Durie, 1996, both herein incorporated by reference).

Leutinizing-releasing hormone agents or gonadotropin-releasing hormone antagonists are used primarily in the treatment of prostate cancer. These include Leuprolide Acetate and Goserelin Acetate. They prevent the biosynthesis of steroids in the testes.

Anti-hormonal antigens include antiestrogenic agents such as Tamoxifen, Antiandrogen agents such as Flutamide, and Antiadrenal agents such as Mitotane and Aminoglutethimide.

ODC (or ornithine decarboxylase) inhibitors inhibit cancerous and pre-cancerous cell proliferation by depleting or otherwise interfering with the activity of ODC, the rate limiting enzyme of polyamine biosynthesis important to neoplastic cell growth. In particular, polyamine biosynthesis wherein ornithine is converted to the polyamine, putrescine, with putrescine being subsequently by converted to spermidine and spermine appears to be an essential biochemical event in the proliferation of neoplastic growth in a variety of cancers and cancer cell lines and the inhibition of ODC activity or depletion of ODC in such neoplastic cells has been shown to reduce polyamine levels in such cells leading to cell growth arrest; more differentiated cell morphology and even cellular senescence and death. In this regard, ODC or polyamine synthesis inhibitors are considered to be more cytotoxic agents functioning to prevent cancer reoccurrence or the conversion of pre-cancerous cells to cancerous cells than cytotoxic or cell killing agents. A suitable ODC inhibitor is eflornithine or $\alpha$-difluoromethyl-ornithine, an orally available, irreversible ODC inhibitor, as well as a variety of polyamine analogs which are in various stages of pre-clinical and clinical research.

Other cytotoxics include agents which interfere or block various cellular processes essential for maintenance of cellular functions or cell mitosis as well as agents which promote apoptosis. In this regard, hydroxyurea appears to act via inhibitors of the enzyme ribonucleotide reductase whereas asparaginase enzymatically converts asparagine into non-functional aspartic acid thereby blocking protein synthesis in a tumor.

Chemotherapeutic agents which are particularly useful in the combination treatment according to the invention include Tubulin interactive agents such as Paclitaxel and Docetaxel; DNA interactive agents such as Cyclophosphamide, Chlorambucil, Cisplatin and Doxorubicin; and antimetabolites such as 5-Fluorouracil and Methotrexate. Preferred chemotherapeutic agents for use in the combination treatment of the invention include Paclitaxel and Cyclophosphamide. When used in the treatment methods of the present invention, it is contemplated that the chemotherapeutic agent of choice can be conveniently used in any formulation which is currently commercially available, and at dosages which fall below or within the approved label usage for single agent use, it being understood that in the combination treatment according to the invention, the effectiveness of the chemotherapeutic agent is enhanced, allowing for corresponding lower dosages.

C. Ionizing Radiation

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art. The amount of ionizing radiation needed in a given cell generally depends on the nature of that cell. Means for determining an effective amount of radiation are well known in the art. Used herein, the term "an effective dose" of ionizing radiation means a dose of ionizing radiation that produces an increase in cell damage or death when given in conjunction with the isocoumarin derivatives of the invention, optionally further combined with a chemotherapeutic agent.

Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Any suitable means for delivering radiation to a tissue may be employed in the present invention, in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

D. Treatment Methods

Tumors that can be suitably treated with the methods of the present invention include; but are not limited to, tumors of the brain (glioblastomas, medulloblastoma, astrocytoma, oligodendroglioma, ependymomas), lung, liver, spleen, kidney, lymph node, small intestine, pancreas, blood cells, colon, stomach, breast, endometrium, prostate, testicle, ovary, skin, head and neck, esophagus, bone marrow, blood and other tissue. The tumor may be distinguished as metastatic and non-metastatic.

The treatment with the isocoumarin derivatives may precede or follow irradiation and/or chemotherapy by intervals ranging from seconds to weeks and/or be administered concurrently with such treatments. In embodiments where the isocoumarin derivative and irradiation and/or chemotherapy are applied separately to the cell, steps should be taken to ensure that a significant period of time does not expire between the time of each delivery, such that the combination of the two or three treatments would still be able to exert an advantageously combined effect on the cell. In such instances, it is contemplated that one would contact the cell with the treatment agents or modalities within amount 0.1 to 25 h of each other and, more preferably, within about 1 to 4 h of each other, with a delay time of only about 1 h to about 2 h being most preferred. In some situations, it is desirable to extend the time period of treatment significantly, however, where several days (2, 3, 4, 5, 6 or 7) or several weeks (1, 2, 3, 4, 5, 6, 7 or 8) lapse between the respective administrations. In any case, the invention contemplates that the isocoumarin derivatives may be given before, after or even simultaneously with the ionizing radiation and/or chemotherapeutic agent.

In one preferred embodiment of the method of the invention, the isocoumarin derivative, for example, NM-3, is administered on a periodic basis (either weekly or daily) for several weeks (at least 3 weeks) prior to administration of either the ionizing radiation or the chemotherapeutic agent. In another embodiment, the extended administration of the isocoumarin derivative can be followed by multiple administrations of radiation doses or doses of the chemotherapeutic agent. Further, if multiple doses of radiation and/or chemotherapy are used on an intermittent basis, the isocoumarin derivative can be administered in the rest periods when no radiation or chemotherapy are being given. It is also anticipated that additional benefit can be achieved by combining the administration of an isocoumarin derivative of the invention with chemotherapy followed by one or more doses of radiation. In this case, the three treatments can be given on a repeated basis with appropriate rest periods until the desired treatment effects are achieved.

In the methods of the present invention, the actual dosage of isocoumarin derivative employed will depend on a variety of factors including the type and severity of cancer being treated, and the additive or synergistic treatment effects of the isocoumarin derivatives and the other treatment modality or modalities selected. Generally, for the isocoumarin derivatives, a dosage of between about 0.1 milligrams (mg) per kilogram (kg) of body weight and about 400 mg per kg of body weight is suitable in the treatment methods of the present invention. Preferably, from about 0.5 mg to about 150 mg/kg body weight is used as the dosage level where multiple administrations of isocoumarin derivatives are given before the dosage with ionizing radiation and/or chemotherapeutic agent.

E. Biological Effects

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cytotoxicity of NM-3 Toward Tumor Cells

To determine the extent to which NM-3 [2-(8-hydroxy-6-methoxy-1-oxo-1H-2-benzopyran-3-yl) propionic acid] inhibited the proliferation of, or was cytotoxic toward, human tumor cells and normal mouse cells, a variety of cell lines were grown in the presence of NM-3. The human cell lines used were K562 (leukemia cells), HT29 (colon tumor cells) HT1080 (reticulum blast sarcoma cells), and MCF7 (breast tumor cells). The mouse cells used were NIH3T3 cells (fibroblasts). All cell lines were cultured in 96-well plates to a density of $2–5 \times 10^3$ cells/well. Culture medium (RPMI 1640 plus 10% FBS) alone or containing NM-3 at one of several concentrations tested was then added to the cultures which were allowed to grow for an additional 3 days. To assess cell growth, 10 µl of WST-1 reagent (a chromogenic substrate for living cells) was added to each well and incubation continued for 3 hrs at 37° C. Absorbance at 450 nm was then determined using a plate reader. For each cell type, the $IC_{50}$ for NM-3 is reported in table 1. Since all $IC_{50}$s were found to be greater than 100 µg/ml, these results indicated that the in vivo anti-tumor activity of NM-3 did not result from direct inhibition of tumor cell growth.

TABLE 1

| Cells | $IC_{50}$ µg/ml) |
|---|---|
| K562 | 250 |
| MKN28 | 175* |
| PC6 | >500 |
| MCF7 | 223 |
| HT29 | >300 |
| HT1080 | 300 |
| NIH3T3 | >100 |

*The values are somewhat low due to the influence of DMSO.

EXAMPLE 2

Effects of NM-3 on Ehrlich Solid Tumor Growth

To determine the antitumor effect of NM-3 on growth of a solid tumor in vivo, $4 \times 10^6$ Ehrlich carcinoma cells per mouse were subcutaneously transplanted into ICR mice (female, 6 weeks old) in the inguinal area. NM-3 was continuously administered via the oral route for 14 days. Tumor weights were then measured on day 15 (Table 2). Whereas tumors from control animals grew to an average size of 1229 mg, tumors from animals treated with 1.25 to 5 mg/kg NM-3 were significantly reduced in size. Tumors from animals receiving the lowest dose of NM-3 (0.63 mg/kg) were also reduced in size but were not significantly different from control values. Thus, NM-3 treatment is associated with a significant reduction in the growth of solid tumors.

TABLE 2

Antitumor effect of NM-3 on Ehrlich Carcinoma

| Dose (mg/kg, p.o.) | Schedule (days) | Mean Tumor Weight (mg ± S.D.) | Inhibition (%) | t-test[a] (p) |
|---|---|---|---|---|
| 0 | — | 1229.1 ± 549.7 | 0.0 | — |
| 5 | 1~14 | 589.7 ± 338.3 | 52.0 | <0.05 |
| 2.5 | " | 519.5 ± 319.3 | 57.7 | <0.01 |
| 1.25 | " | 497.7 ± 265.5 | 59.5 | <0.01 |
| 0.63 | " | 822.5 ± 376.2 | 33.1 | n.s. |

[a]Compared with untreated control mice by Student's t-test

EXAMPLE 3

Effects of NM-3 on Experimental Tumor Metastasis

To determine the antitumor effect of NM-3 on metastatic tumor growth, B16-BL6 melanoma cells ($2 \times 10^4$ cells per mouse) were transplanted into BDF1 mice (female, 5 weeks old) via the tail vein. NM-3 was continuously administered via the oral route for 13 days following transplantation of the tumor cells. On day 14, the lungs were excised and fixed, and the metastatic colony numbers were counted. The animals treated with NM-3 (0.08 to 5 mg/kg) experienced a reduction in the number of pleural metastatic foci compared to control animals (Table 3). These results suggest that NM-3 may impart an antitumor effect on the growth of small tumors that arise from tumor metastasis.

TABLE 3

| Dose (mg/kg, p.o.) | Schedule (days) | Number of lung metastases (Mean ± S.D.) | (Range) | Inhibition (%) |
|---|---|---|---|---|
| 0 | — | 84.2 ± 19.1 | (114–51) | 0.0 |
| 5.0 | 1~13 | 68.4 ± 16.9 | (90–47) | 18.8 |
| 1.25 | " | 72.6 ± 20.6 | (106–43) | 13.8 |
| 0.31 | " | 64.0 ± 23.8 | (107–38) | 24.0 |
| 0.08 | " | 88.7 ± 16.1 | (109–62) | −5.3 |

EXAMPLE 4

Effect of NM-3 in Combination Therapy with Cyclophosphamide on Colon 26 Adenocarcinoma To determine the effect on tumor growth of NM-3 treatment combined with simultaneous cyclophosphamide treatment, colon 26 adenocarcinoma cells ($5 \times 10^4$ cells per mouse) were subcutaneously transplanted into BALB/c mice (female, 7 weeks old) in the inguinal area. NM-3 was continuously orally administered from day 1 to day 72 after the transplantation except on day 14 when cyclophosphamide was dosed. The mean survival days were recorded and reported in Table 4, below. While cyclophosphamide treatment alone resulted in significantly extended survival times (145% of control), NM-3 treatment alone (1 or 5 mg/kg) did not increase survival times. When animals were administered both treatments, survival times significantly increased relative to the control value, and were significantly greater than cyclophosphamide treatment alone in the 5 mg/kg group.

Thus, these results suggest that NM-3 treatment significantly augments the ability of cyclophosphamide to inhibit tumor growth, which resulted in a concomitant increase survival time.

EXAMPLE 6

NM-3 Increases the Sensitivity of Endothelial Cells to Radiation

Human umbilical vein endothelial cells (HUVEC) were exposed to a constant amount of gamma radiation in the presence or absence of various concentrations of NM-3 in the culture medium. The numbers of HUVEC colonies that formed following the different treatments were recorded and normalized to the number of colonies formed under control (no NM-3) conditions and the results are shown in FIG. 1. NM-3 treatment decreased HUVEC colony formation is dose dependent manner, with an $ED_{50}$ of approximately 1 μg/ml (see FIG. 1A). For comparison, HUVEC cells were treated with either angiostatin or endostatin, two additional anti-angiogenic proteins. Neither angiostatin nor endostatin inhibited HUVEC growth to the extent of NM-3 (see FIGS. 1B and 1C).

Figure 2:
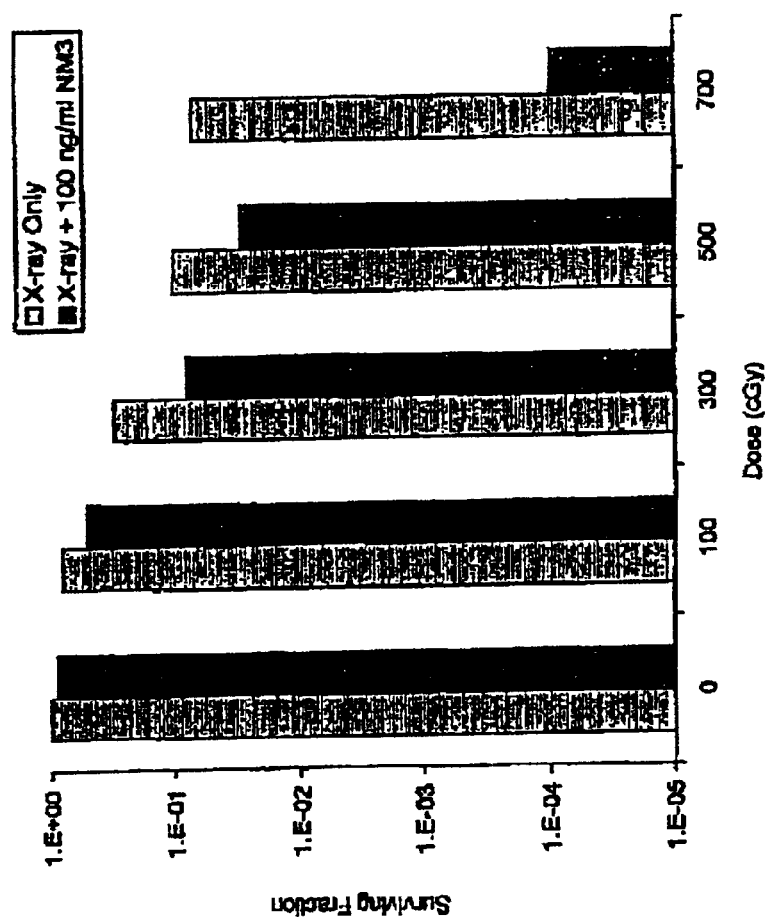
FIG. 2 is a graph showing the effects of gamma radiation and the combination of gamma radiation and NM-3 on the number of human umbilical vein endothelial cell (HUVEC) colonies formed following treatment.

In another study of HUVEC radiation sensitivity, cells were treated with NM-3 (100 ng/ml) 1 hr prior to exposure of the cells to increasing doses of gamma irradiation (X-rays). The numbers of HUVEC colonies that formed following the different treatments were recorded and normalized to the number of colonies formed under control conditions (see FIG. 2). Increasing doses of X-rays in the absence of NM-3 decreased HUvEC colony survival to a minimal value of 10% survival at the highest dose tested. In the presence of NM-3, HUVEC colony survival decreased to 0.01% of the initial living cells at the highest X-ray dose. Therefore, NM-3 treatment increased the sensitivity of these cells to X-ray induced lethality by approximately 1000-fold at the highest X-ray dose.

EXAMPLE 7

NM-3 Increases the Radiation Sensitivity of Lewis Lung Carcinoma, in vivo

To determine whether NM-3 treatment increases the radiation sensitivity of tumors in vivo, Lewis Lung carci-

TABLE 4

| Cyclophosphamide (300 mg/kg, i.v. day 14) | NM-3 | Dose (mg/kg, p.o.) | Schedule (day) | Mean Survival Days (days ± S.D.) | T/C (%) | t-test[a] (p) |
|---|---|---|---|---|---|---|
| — | — | — | — | 33.0 ± 14.2 | 100.0 | — |
| ± | — | — | — | 47.9 ± 13.9 | 145.1 | <0.05 |
| — | ± | 5 | 1–13, 15–72 | 23.5 ± 3.7 | 71.2 | n.s. |
| — | ± | 1 | " | 33.9 ± 13.6 | 102.7 | n.s. |
| ± | ± | 5 | " | 55.0 ± 14.7 | 166.7 | <0.01 |
| ± | ± | 1 | " | 57.8 ± 16.6 | 175.0 | <0.01 |

[a]Compared with untreated control mice by Student's t-test

EXAMPLE 5

Effect of NM-3 in Combination Therapy with Cyclophosphamide on IMC Carcinoma To determine the effect on IMC carcinoma growth of NM-3 treatment combined with simultaneous cyclophosphamide treatment, IMC carcinoma cells ($1 \times 10^6$ cells per mouse) were subcutaneously transplanted into CDF1 mice (female, 10 weeks old) in the inguinal area. NM-3 which was dissolved using 5% DMSO+Tween80, was continuously orally administered from day 1 to day 41 after transplantation except on day 14, when cyclophosphamide (300 mg/kg) was injected intravenously. Tumor weights were measured after the excision of tumors on day 42 and are shown in Table 6. Cyclophosphamide treatment alone significantly reduced tumor weight by 70.7%, while NM-3 treatment alone did not significantly reduce tumor weight. Tumor weights were also significantly reduced by the combination treatment of cyclophosphamide and NM-3. In the case of the low dose of NM-3 (1 mg/kg), tumor weight was significantly reduced relative to the tumors from cyclophosphamide-treated animals. Thus, anti-tumor activity of cyclophosphamide could be augmented by NM-3 treatment.

TABLE 5

| Cyclophosphamide (300 mg/kg, i.v. day 14) | NM-3 (mg/kg, p.o.) | Schedule (day) | Solid Weight mg ± S.D. | Inhibition (%) | t-test[a] (p) |
|---|---|---|---|---|---|
| — | — | — | 12350 ± 2717.8 | 0.0 | — |
| ± | — | — | 3620.4 ± 1406.3 | 70.7 | <0.01 |
| — | 5 | 1–13, 15–41 | 10792.4 ± 2979.7 | 12.6 | n.s. |
| — | 1 | " | 11,093.0 ± 2040.6 | 10.2 | n.s. |
| ± | 5 | " | 2798.3 ± 654.0 | 77.3 | <0.01 |
| ± | 1 | " | 2028.9 ± 782.2 | 83.6*[b] | <0.01 |

Figure 3:
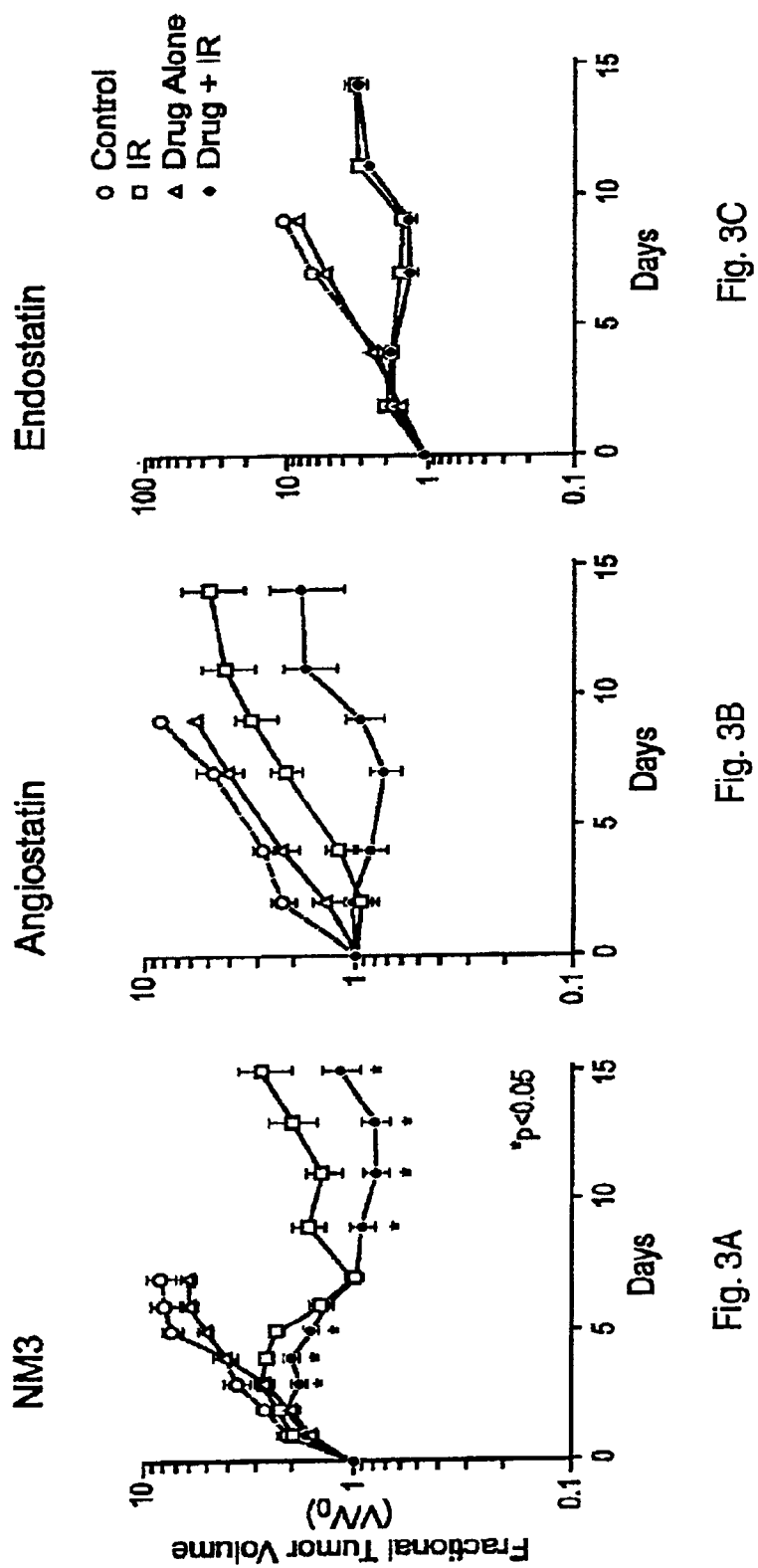
FIG. 3 is a series of three graphs showing the effects of gamma radiation combined with either NM-3, angiostatin or endostatin on Lewis Lung Carcinoma tumor growth in C57B46 mouse xenographs.

[a]Compared with untreated control mice by Student's t-test
[b]Compared with Cyclophosphamide control mice by Student's t-test noma (LLC) tumors were established in C57BL/6 female mice (Frederick Cancer Research Institute) prior to NM-3 and radiation treatment. LLC cells (1×10$^6$ cells) were injected in the right hind limb of the mice and tumors were allowed to grow a volume of 250–350 mm$^3$. Tumor volumes were determined by direct measurements with calipers calculated by the formula: V=length×width×depth/2. Mice were then divided into groups and treated with NM-3 (100 mg/kg total) or PBS for two days before beginning radiation therapy. Animals then received NM-3 (25 mg/kg/day, i.p.) or PBS approximately four hours prior to radiation treatment. Tumors were irradiated using a GE Maxitron X-ray generator operating at 150 kV, 30 mA, using a 1 mm aluminum filter at a dose rate of 188 cGy/minute. Mice were shielded with lead except for the tumor-bearing area in the hind limb. Treatments and tumor measurements continued for a period of 17 days (see FIG. 4). X-ray treatment alone resulted in a highly significant delay in tumor growth. Whereas control tumors reached 8 initial tumor volumes (Vo) after 8 days, X-ray treated tumors required 16 days to grow to this size. When NM-3 treatment was added to the radiotherapy, further tumor growth was markedly reduced and only began to appear after 15 days. This result was not due to a direct antitumor effect of NM-3 because NM-3 alone did not inhibit tumor growth at all. These results, as shown in FIG. 3A, indicate that NM-3 treatment dramatically enhances the sensitivity of internally growing tumors to subsequent radiation therapy. For comparison, data are plotted with two additional anti-angiogenic drugs, antiostatin and endostatin (see FIGS. 3B and 3C). Angiostatin showed some radiation sensitization, whereas endostatin did not.

In a second similar experiment, X-ray treatment and X-ray treatment combined with NM-3 treatment were again compared for their relative abilities to inhibit LLC tumor growth. However, the treatment period was extended to determine whether either treatment regimen was able to initiate complete tumor cures. Animals were injected with 106 cells initially and starting tumor volumes were approximately 500 mm$^3$. Tumors were irradiated on days 2 and 4 with 20 Gy X-irradiation. NM-3 was administered at 25 µg/kg daily over the first four days. The tumors of both groups increased slightly in size following initiation of treatment and then began to decrease after several days. Tumors in the X-ray only group began to increase steadily in size after the 10$^{th}$ day of continuous treatment. In contrast, tumors in the NM-3+X-ray group continued to decrease in size following the initial growth phase. Ultimately, 9 of 10 animals receiving NM-3+X-ray treatment experienced a complete cure while only 3 of 10 animals were cured by the X-ray treatment alone.

In summation, these results demonstrate that NM-3 holds significant therapeutic promise as a radiation sensitizing agent. In vitro experiments document the enhanced sensitivity of endothelial cells to radiation as a result of NM-3 exposure and suggest a rationale for treating human tumors. The in vivo tumor studies show that this strategy of preventing tumor growth can be an effective treatment.

EXAMPLE 8

In Vivo Study Designed to Evaluate Antitumor Activity of NM-3 in Combination with Paclitaxel Against the MDAMB-435 Human Breast Orthotopic Model in Nude Mice In order to determine the effect of the combination of NM-3 with the cytotoxic drug, paclitaxel on human breast tumor xenografts, female NCRNU nude mice were implanted with MDAMB-435 cells into the subaxillary mammary fat pad. NM-3 was administered via intraperitoneal (i.p.) injection daily at doses ranging from 10–100 mg/kg; paclitaxel was administered via i.p. injection every 7 days, starting on day 0, at 10 mg/kg.

Figure 4:
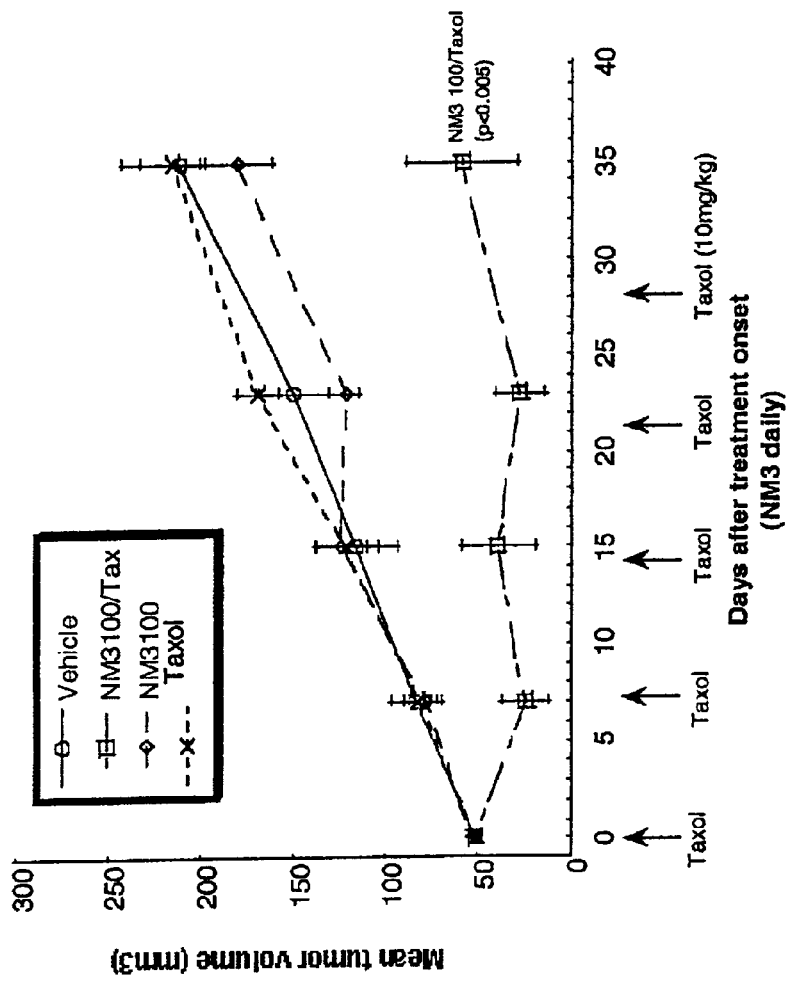
FIG. 4 is a graph showing the tumor growth inhibitory effect of NM-3 alone, and in combination with Paclitaxel on 50 mm$^3$ pre-existing MDAAMB435 human breast tumor xenografts in a nude mouse model system.

As a single agent, paclitaxel showed minimal effect at 10 mg/kg, given every 7 days via i.p. injection, whereas 20 mg/kg had a significant effect on tumor growth inhibition. FIG. 4 shows mean tumor volumes plotted against time, and the results of this study are summarized in Table 6, below. NM-3 administered as a single agent at 100 mg/kg; i.p. daily resulted in a tumor growth inhibition (TGI) of 15.29%. The addition of paclitaxel at 10 mg/kg q7d resulted in a TGI of 72.35%. There were 5 complete responses. Paclitaxel alone or in combination with NM-3 at the lower dose of 10 mg/kg; i.p. daily resulted in no tumor growth inhibition. No substantial weight loss was observed in any of the groups throughout the protocol.

TABLE 6

| Taxol | NM-3 (mg/kg; I.P. daily) | n | Final Tumor Wt. (mg) +/- SEM | % Tumor Growth Inhibition | Mice with Complete Shrinkage | t-test (p) |
| --- | --- | --- | --- | --- | --- | --- |
| 0 | 0 | 9 | 212.5 ± 30.92 | — | 0 | — |
| 10 mg/kg q7d | 10 | 9 | 228.8 ± 26.35 | — | 0 | — |
| 10 mg/kg q7d | 100 | 9 | 58.75 ± 29.91 | 72.35 | 5 | <0.005 |
|  | 100 | 9 | 180.0 ± 18.13 | 15.29 | 0 | n.s. |
| 10 mg/kg q7d | 0 | 9 | 215.6 ± 19.73 | — | 0 | — |

Figure 5:
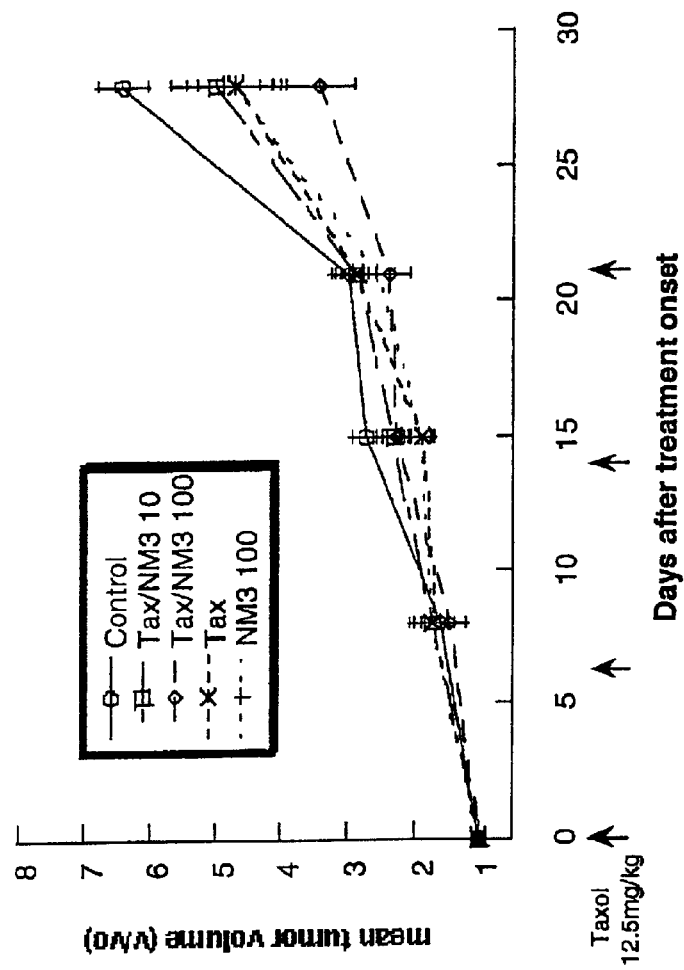
FIG. 5 is a graph showing the tumor growth inhibitory effect of NM-3 alone, and in combination with Paclitaxel on 100 mm$^3$ pre-existing MDAAMB435 human breast tumor xenografts in a nude mouse model system.

In a second study, treatment was initiated when tumor volumes reached 100 mm$^3$. Paclitaxel was administered at the fixed dose of 12.5 mg/kg, q7d and NM-3 was dosed at 10 and 100 mg/kg, i.p. daily for 28 days. FIG. 5 shows mean tumor volume ratios plotted against time. The results of this study are summarized in Table 7, below. NM-3 alone given at a daily dose of 10 mg/kg had no significant tumor growth inhibition, whereas at NM-3 at 100 mg/kg resulted in a TGI of 26.67%. Paclitaxel administered alone at 12.5 mg/kg, q7d resulted in a TGI of 26.52%, and when combined with NM-3, the TGI was 46.10%. All treatments were well tolerated, with no substantial weight loss being observed.

TABLE 7

| Taxol | NM-3 (mg/kg, I.P. daily) | n | Final Tumor Ratio (V/Vo) +/− SEM | % Tumor Growth Inhibition | Mice with Complete Shrinkage | t-test (p) |
|---|---|---|---|---|---|---|
| 0 | 0 | 9 | 6.41 ± 0.40 | — | 0 | |
| 12.5 mg/kg q7d | 10 | 9 | 4.99 ± 0.66 | 22.15 | 0 | n.s. |
| 12.5 mg/kg q7d | 100 | 9 | 3.45 ± 0.54 | 46.10 | 0 | <0.001 |
| | 100 | 9 | 4.70 ± 0.56 | 26.67 | 0 | <0.03 |
| 12.5 mg/kg q7d | 0 | 9 | 4.71 ± 0.76 | 26.52 | 0 | <0.03 |

Figure 6:
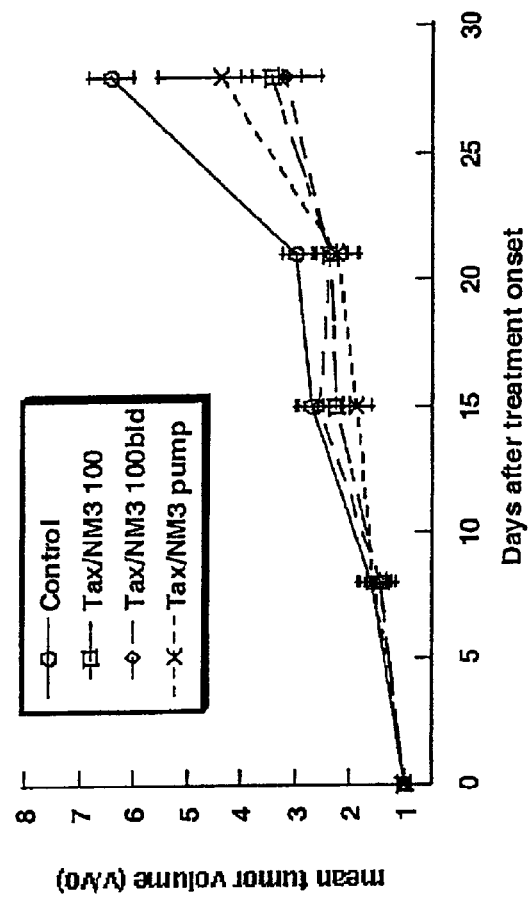
FIG. 6 is a graph showing the effect of different dosing regimens of NM-3 on the tumor growth inhibitory effect of NM-3 against 100 mm$^3$ pre-existing MDAAMB435 human breast tumor xenografts in a nude mouse model system.

A comparison was also made between different delivery routes of NM-3 in the combination studies. NM-3 given i.p. daily, bid, and continuously using Alzet mini osmotic pumps in combination with paclitaxel was evaluated for effectiveness in reducing tumor growth. FIG. 6 shows mean tumor volume ratios plotted over time, and Table 8, below, summarizes the data. Bid dosing with NM-3 was more effective than daily dosing, when combined with paclitaxel. However, continuous delivery using mini-pumps implanted subcutaneously was not as effective as i.p. delivery.

TABLE 8

| Taxol | NM-3 (mg/kg) | Route | n | Final Tumor Ratio (V/Vo) +/− SEM | % Tumor Growth Inhibition | t-test (p) |
|---|---|---|---|---|---|---|
| 0 | 0 | | 9 | 6.41 ± 0.40 | — | |
| 12.5 mg/kg q7d | 100 | i.p. daily | 9 | 3.45 ± 0.54 | 46.10 | <0.001 |
| 12.5 mg/kg q7d | 100 | i.p. bid | 9 | 3.172 ± 0.629 | 50.52 | <0.001 |
| 12.5 mg/kg q7d | 100 | Continuous | 9 | 4.386 ± 1.157 | 31.58 | n.s. |

EXAMPLE 9

Antitumor Activity of NM-3 in Combination with 5-Fluorouracil vs. MDAMB-435 Human Breast Orthotopic Model in Nude Mice In order to evaluate the antitumor activity of NM-3 in combination with 5-Fluorouracil (5-FU) vs. MDAMB-435 human breast tumor xenografts, female NCRNU nude mice were implanted with MDAMB-435 cells into the subaxillary mammary fat pad. When the tumors were between 50 and 80 mm$^3$, NM-3 was administered via intraperitoneal (i.p.) injection daily at 10 and 100 mg/kg; 5-FU was administered via i.p. injection on days 0 and 14, at 10 mg/kg. Mice were weighed twice weekly, and tumor measurements were taken by calipers twice weekly. Mice were euthenized at the end of the treatment period. Upon termination, the mice were weighed, sacrificed and their tumors were excised. The mean tumor weight per group was calculated, and the mean treated tumor weight/mean control tumor weight ×100% was subtracted from 100% to give the tumor growth inhibition (TGI) for each group.

Figure 7:
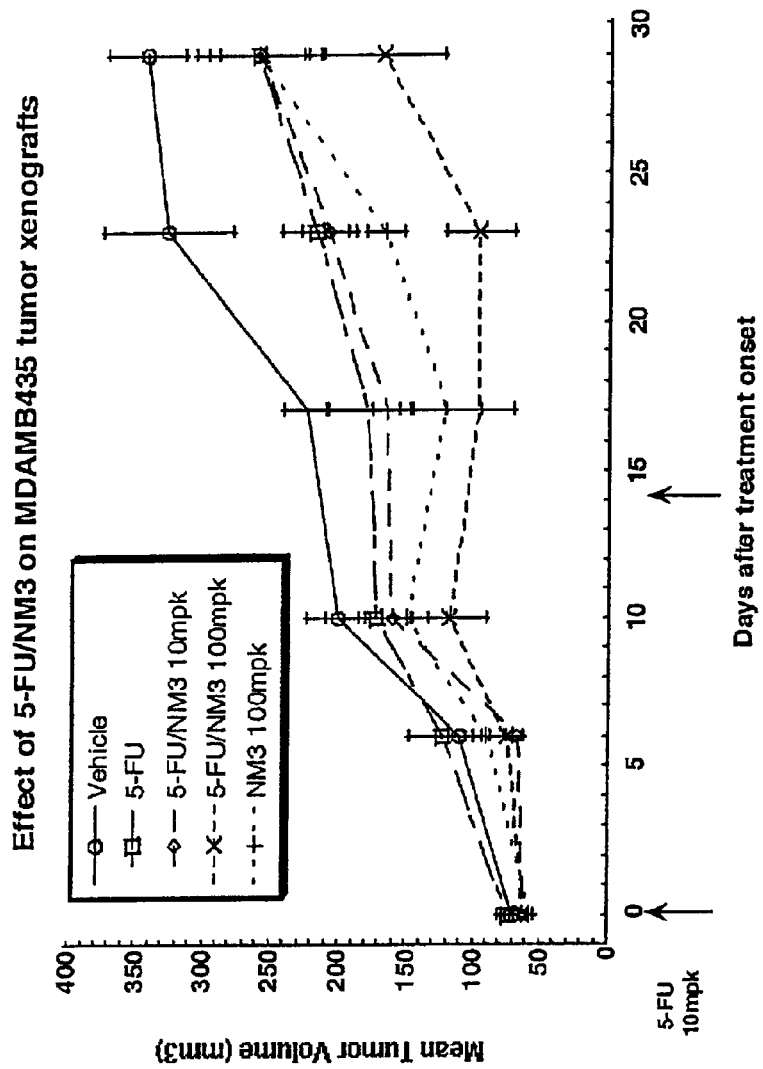
FIG. 7 is a graph showing the tumor growth inhibitory effect of NM-3 alone, and in combination with 5-fluorouracil (5-FU) on 50 mm$^3$ pre-existing MDAAMB435 human breast tumor xenografts in a nude mouse model system.

Initial studies were conducted with 5-FU to determine the optimal dose of this agent when administered in combination with NM-3. When 5-FU was administered at 10 mg/kg, q14d, there was no significant TGI. Animals treated with NM-3 administered as a single agent at 100 mg/kg; i.p. daily had a final mean tumor weight not significantly different than the control group. 5-FU in combination with NM-3 at the dose of 100 mg/kg; i.p. daily resulted in a TGI of 50.80%. FIG. 7 shows mean tumor volume ratios plotted over time, and Table 9, below, summarizes the data. No substantial weight loss was observed in any of the groups throughout the protocol.

TABLE 9

| 5-FU | NM-3 (mg/kg/day) | n | Final Tumor Wt. (mg) +/− SEM | % Tumor Growth Inhibition | t-test (p) |
|---|---|---|---|---|---|
| 0 | 0 | 9 | 341.5 ± 28.70 | 0 | — |
| 10 mpk q14d; 0,14 | 10 | 9 | 257.3 ± 31.06 | 24.66 | 0.08 |
| 10 mpk q14d; 0,14 | 100 | 9 | 168.0 ± 45.6 | 50.80 | 0.01 |
| 0 | 100 | 9 | 259.2 ± 46.99 | 24.1 | 0.17 |
| 10 mpk q14d; 0,14 | 0 | 9 | 259.6 ± 36.22 | 23.98 | 0.12 |

EXAMPLE 10

NM-3 Enhances the Ability of Ionizing Radiation (IR) to Inhibit the Growth of Tumors In Vivo The effects of NM-3 and IR on tumor growth were assessed in Lewis Lung Carcinoma (LLC), Seg-1, and SQ-20B tumors implanted in C57BL/6 nude mice.

Figure 8:
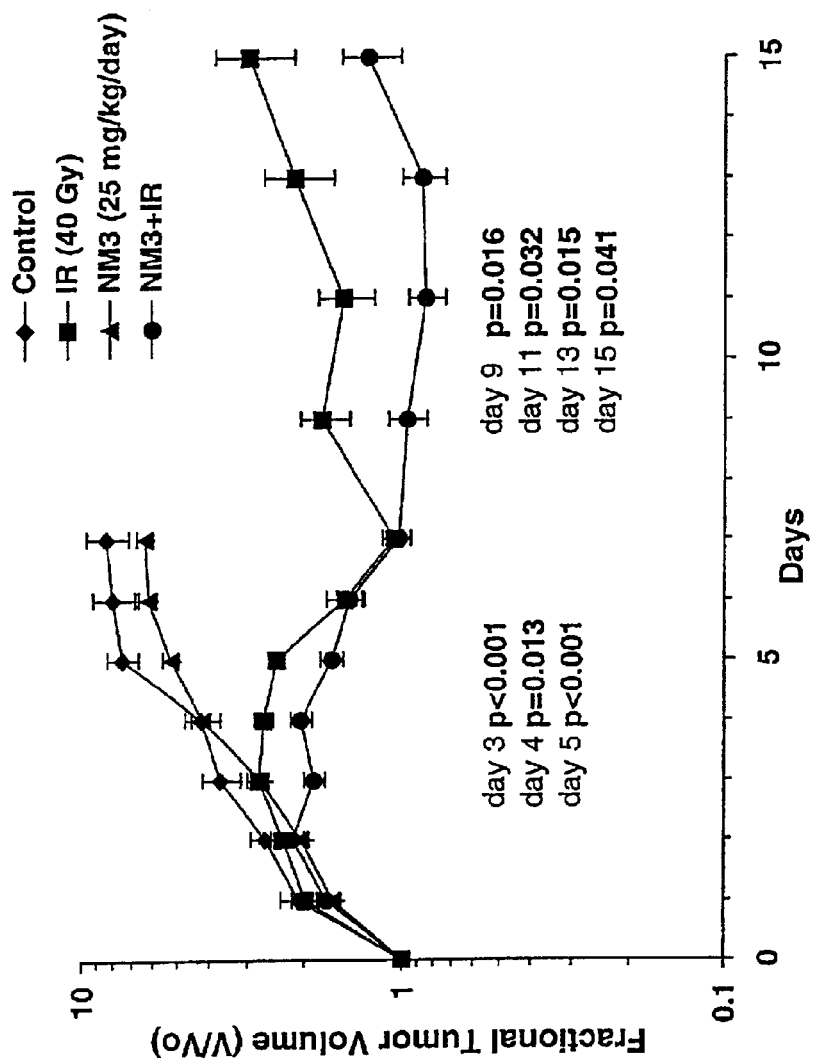
FIG. 8 is a graph showing the effect of NM-3, radiation and the combination on established Lewis Lung Carcinoma tumors in a murine model system.
Figure 9:
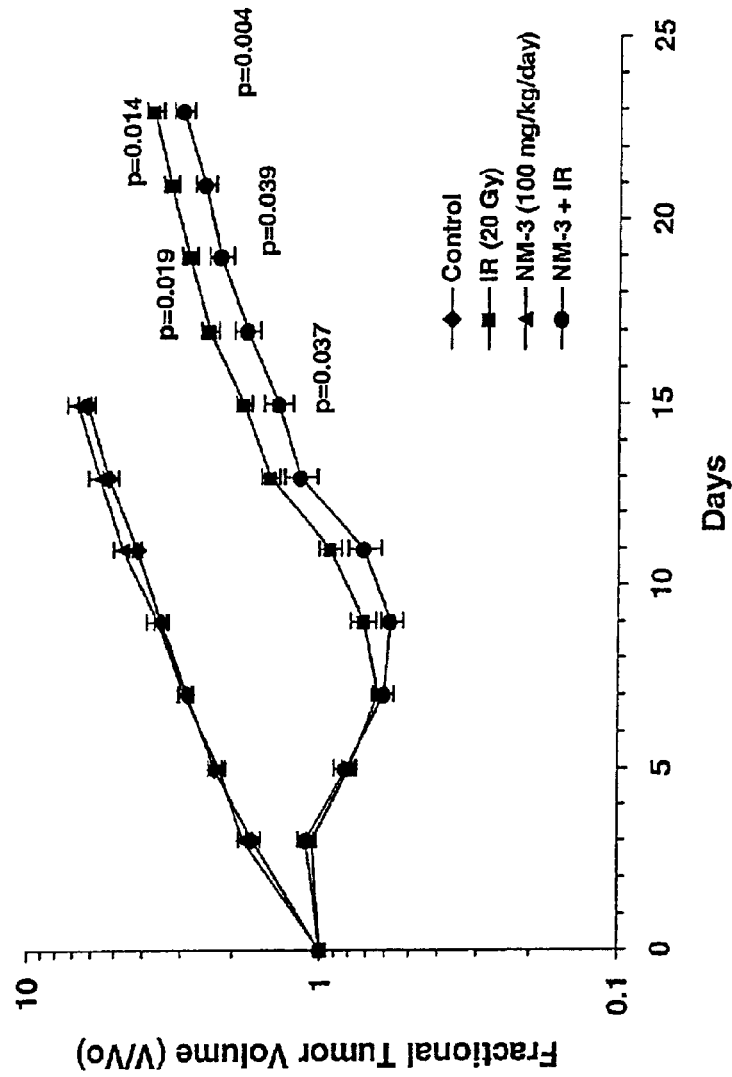
FIG. 9 is a graph showing the effect of NM-3, radiation and the combination of the growth of Seq-1 tumors a nude mouse model.

By day 7, LLC tumors in the control group and the NM-3 group grew to 8.02±1.24 and 6.19±0.44 times original volume, respectively. Animals in these treatment groups were sacrificed on day 7 due to tumor burden. LLC tumors in the IR (20+20 Gy) group initially grew and then regressed to 1.06±0.08 times original volume (day 7). Regression was followed by regrowth to 2.98±0.83 times original volume at day 15 when the experiment was terminated. Combined treatment with NM-3 and IR significantly reduced mean tumor volume when compared with IR alone at day 3, 4, 5, 9, 11, 13 and 15. (FIG. 8A)

Seg-1 tumors in the control group and the NM-3-treated group grew to 6.30±0.42 and 6.74±0.62 times original volume by day 15 at which time the animals were sacrificed due to tumor burden. Tumors in the IR (4 doses of 5 Gy) group initially regressed (0.64±0.03 times original volume, day 7) and then regrew (1.83±0.11, day 15). Combined treatment with NM-3 and IR significantly reduced mean tumor volume at days 15, 17, 19, 21 and 23 when compared with IR treatment alone. (FIG. 8B). The combined treatment group demonstrated a growth delay of 14 days compared to the control group and 3 days compared to IR alone group.

In experiments conducted using SQ-20B tumors, control tumors grew to 5.2±0.94 times original volume by day 20. A similar pattern of tumor growth was observed in the NM-3 alone treatment group (4.3±1.03, day 20). Animals in these two groups were subsequently sacrificed because of tumor burden. Tumors in the IR treatment group (65 Gy) doubled in size by day 6, and regressed to 50% of original volume at day 23. By day 38, IR treated tumors regrew to twice original volume. Animals treated with NM-3 and IR doubled in size by day 6 and then regressed to 77% of original volume at day 23. Unlike the tumors treated with IR alone, tumors receiving combined therapy with NM-3 and IR failed to reach original volume by day 38 (p=0.006, t-test).

NM-3 increased the antitumor effects of IR in three different tumor model systems, both murine and human, as measured by tumor regression.

EXAMPLE 11

Effects of NM-3 in Combination with Dexamethasone or Doxorubicin on MM1.S Human Multiple Myeloma Cells In addition to enhancement of standard chemotherapy and radiotherapy of the isocoumarin compounds of the present invention by inhibition of angiogenesis, enhanced sensitivity may also arise by the isocoumarin compounds acting directly on tumor cells. The effects of NM-3 in combination with dexamethasone (DEX) or doxorubicin (DOX) on MM1.S human multiple myeloma cells were investigated.

NM-3 was dissolved in $Mg^{2+}$ and $Ca^{2+}$ free phosphate buffered saline (PBS) by adding appropriate volume of 10 N NaOH (final pH<7.0). DEX was dissolved in absolute ethanol and diluted with PBS. Final concentration of ethanol in the culture medium was 0.5% or less. DOX was dissolved in PBS.

The human multiple myeloma cell line MM1.S was maintained in RPMI1640 medium supplemented with 10% fetal bovine serum, 100 units/ml penicillin, and 100 µg/ml streptomycin at 37° C. in an atmosphere of 5% CO2 in air. Cells ($3\times10^4$ cells/well) were seeded in 96 well-plates and incubated with increasing concentrations of DEX or DOX in the presence or absence of NM-3. NM-3 was added at concentrations of 0, 50, 100 and 200 µg/ml 2 hours before the addition of DOX or DEX. After 24 hours of DOX or DEX exposure, 10 µl of MTT reagent (Roche Molecular Biochemicals, final concentration 0.5 mg/ml) was added to each well and allowed to incubate for 4 hours. After the incubation, 100 µl of solubilization solution (10% sodium dodecyl sulfate in 0.01M HCl) was added to each well and allowed to incubate overnight. Optical density at 565 nm was determined using a spectrophotometer (Molecular Devices Corp.).

Apoptosis was determined by staining cells with annexin V-FITC and propidium iodide (PI). Cells were treated with DEX in the presence or absence of NM-3. NM-3 was added 2 hours before the addition of DEX. After 24 hours of DEX exposure, cells were washed twice with cold PBS, resuspended in binding buffer (10 mM HEPES/NaOH (pH 7.4), 140 mM NaCl, 2.5 mM CaCl2), and then stained with annexin V-FITC (Clontech Laboratories) and PI (Boehringer-Manheim). Apoptosis was analyzed by using a flow cytometer (EPICS XL-MCL, Coulter Corp). The cultured cells were also subjected to cell cycle analysis. Briefly, cells were washed twice with PBS and fixed with 70% ethanol. Cells were then washed with 0.5 ml PBS and 1.0 ml phosphate-citric acid buffer (0.2 M Na2HPO4 and 0.1 M citric acid (pH 7.8)), treated with 200 µg/ml RNase for 15 min at 37° C., and stained with 50 µg/ml PI for 30 min at room temperature in the dark. Cells were filtered through 35-µm diameter mesh to remove clumps. Nuclear staining was analyzed by a flow cytometer. Cells with fractional DNA content located on DNA frequency histograms to the left of the G1 peak (sub-G1 cells) were identified as apoptotic cells.

Figure 10:
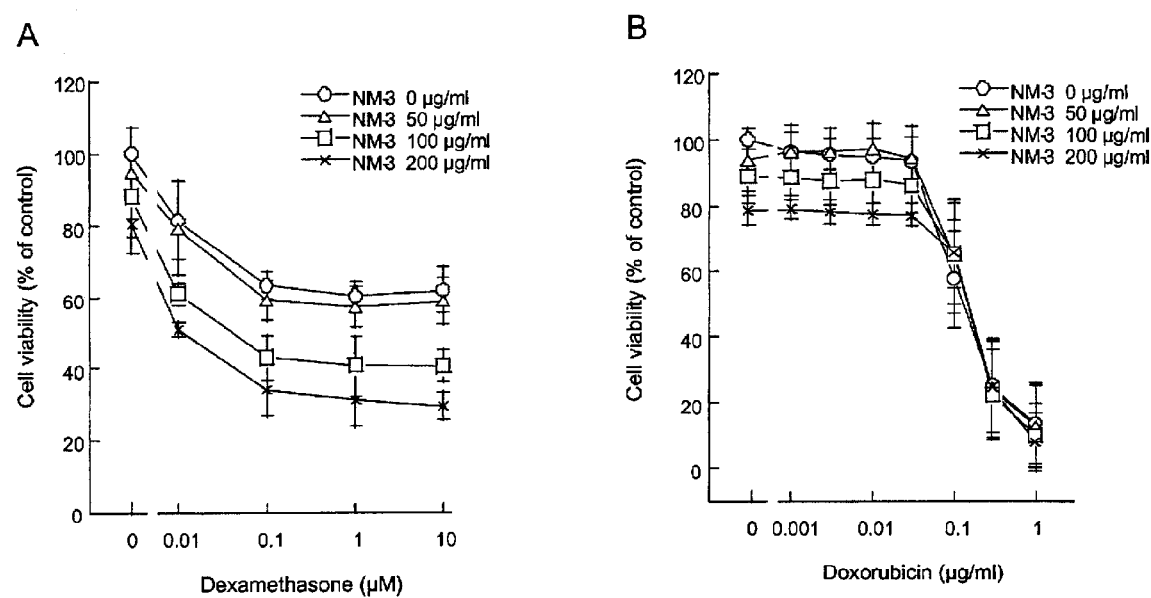
FIG. 10 is a series of two graphs showing the effects of NM-3 on DEX- and DOX-induced cell death in MM1.S cells. Cells were treated with DEX or DOX for 24 hours in the presence or absence of NM-3. Cell viability was assessed by MTT assay. Results represent the mean ±S.E. of three independent experiments.
Figure 11:
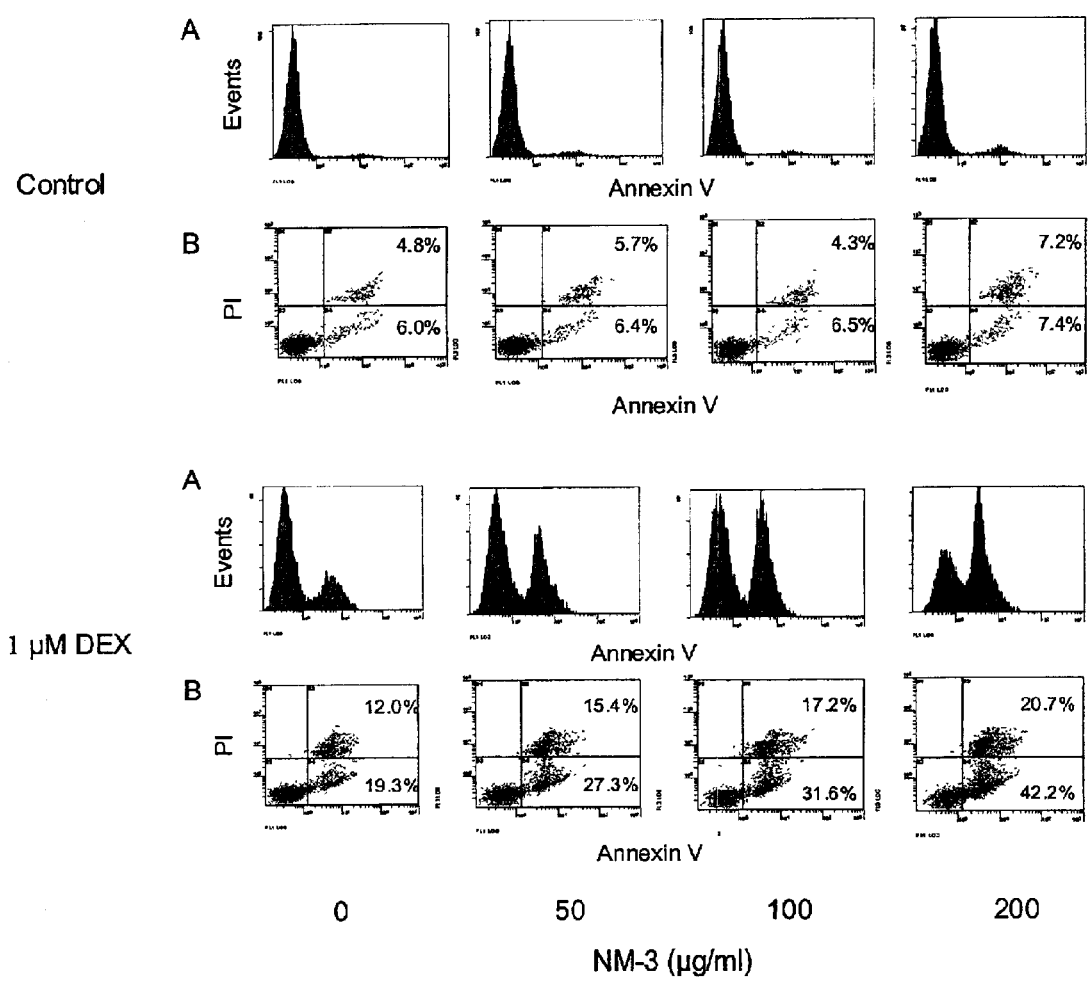
FIG. 11 is a series of graphs showing the effects of NM-3 on DEX- induced apoptosis in MM1.S cells. Cells were cultured without (upper panel) or with (lower panel) 1 μM DEX in the presence or absence of NM-3 for 24 hours.
Figure 12:
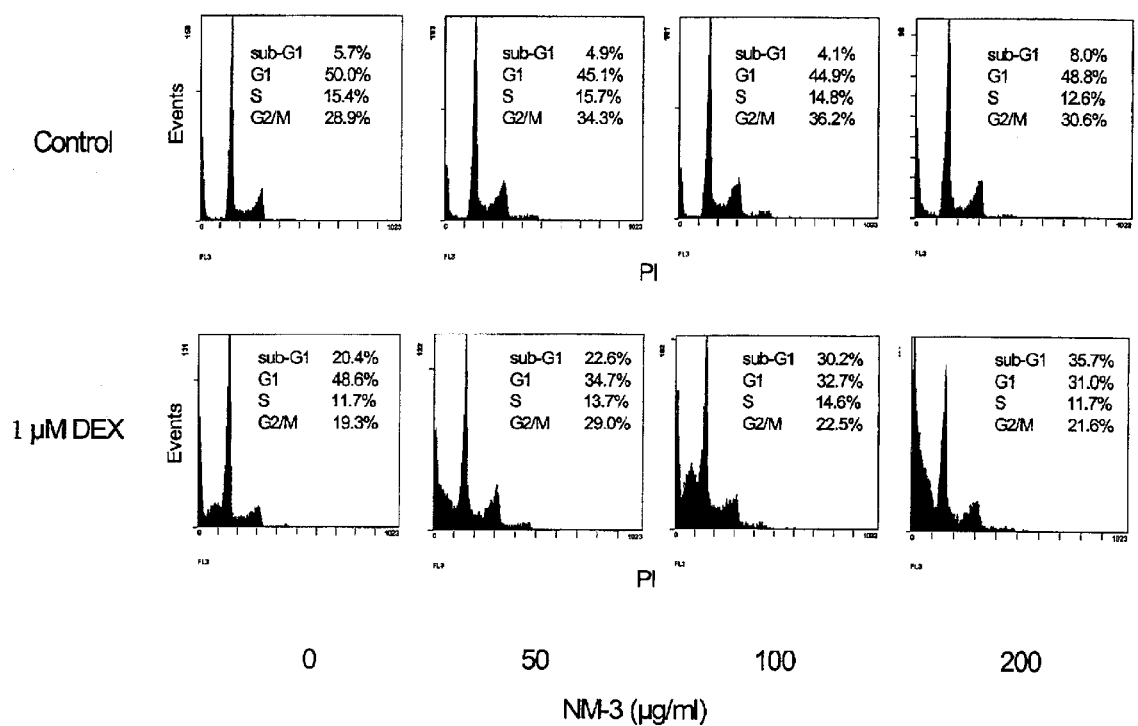
FIG. 12 is a series of graphs showing the effects of NM-3 and DEX on cell cycle profiles in MM1.S cells. Cells were treated with DEX (1 μM) in the presence or absence of NM-3 for 24 hours. The cell cycle profile was evaluated by propidium iodide (PI) staining using a flow cytometer.

The effect of NM-3 on DEX and DOX induced cell death in MM1.S cells is shown in FIG. 10. NM-3 alone (50–200 µg/ml) only slightly decreased the cell viability. NM-3 potentiated DEX-induced cell death in a concentration-dependent manner, but not DOX-induced cell death. The effect of NM-3 on DEX-induced apoptosis in MM1.S cells is shown in FIG. 11. NM-3 alone (50–200 µg/ml) did not change the population of cells positive for annexin V and PI (apoptotic cells). DEX induced a significant increase in the population of apoptotic cells, which was further enhanced by pretreatment with NM-3 in a concentration-dependent manner. FIG. 12 shows the effect of NM-3 and DEX on MM1.S cell cycle profiles. Although NM-3 alone (50–200 µg/ml) showed only nominal effects on the cell cycle profiles, NM-3 increased DEX-induced sub-G1 cells (apoptotic cells) in a concentration-dependent manner.

These findings show that NM-3 potentiated a DEX-induced, but not a DOX-induced, decrease in the cell viability and that treatment of MM1.S cells with NM-3 and DEX significantly increased apoptotic cell death by approximately 2-fold as determined by sub-G1 DNA content and Annexin-V staining assay. Thus, in addition to anti-angiogenic activity, NM-3 is capable of enhancing DEX-induced apoptosis in human multiple myeloma cells.

EXAMPLE 12

Effects of NM-3 in Combination with Dexamethasone on RPM18226 and U266 Human Multiple Myeloma Cells The effects of NM-3 in combination with dexamethasone on the viability of RPM18662 and U266 human multiple meyeloma cells were investigated. Experimental conditions were as described in Example 11, with the exception that cells were seeded at $6\times10^3$ cells/well and the cells were incubated with the appropriate concentrations of NM-3 and DEX for either 48 or 72 hours prior to addition of the MTT reagent.

Figure 13:
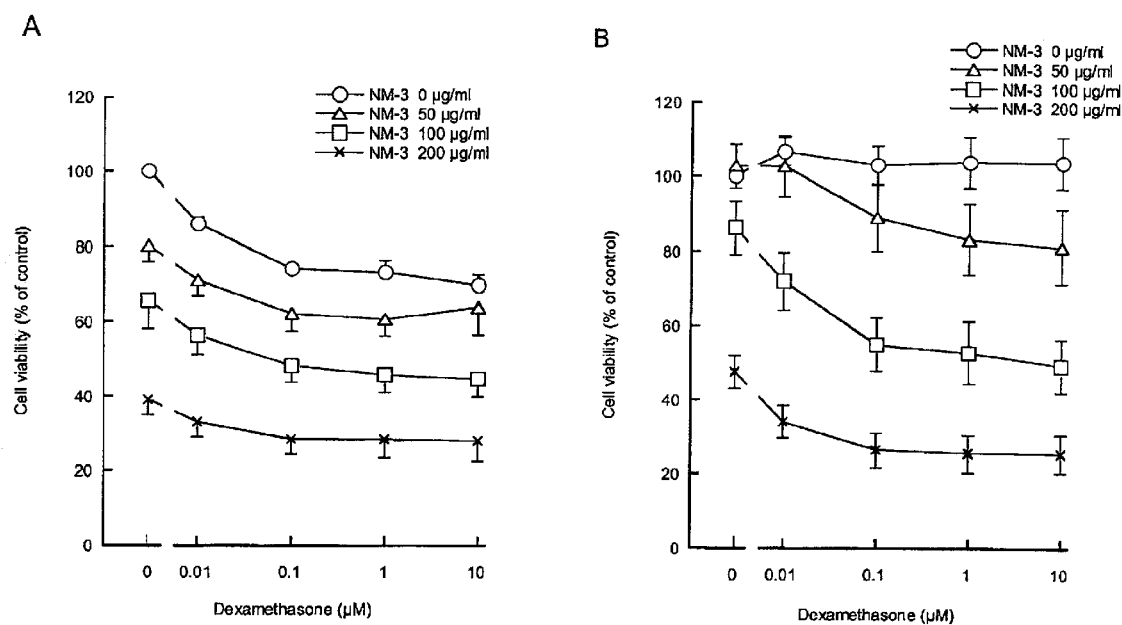
FIG. 13 is a series of two graphs showing the effects of NM-3 on DEX-induced cell death in RPMI8662 cells. Cells were treated with DEX for 48 or 72 hours in the presence or absence of NM-3. Cell viability was assessed by MTT assay. Results represent the mean ±S.E. of three independent experiments.
Figure 14:
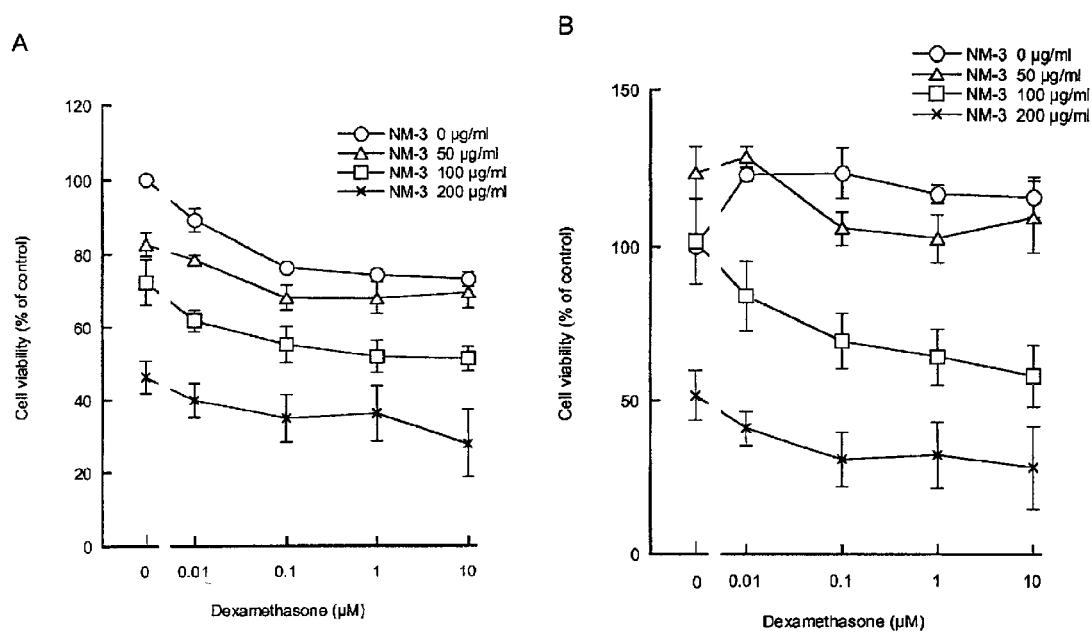
FIG. 14 is a series of two graphs showing the effects of NM-3 on DEX-induced cell death in U266 cells. Cells were treated with DEX for 48 or 72 hours in the presence or absence of NM-3. Cell viability was assessed by MTT assay. Results represent the mean ±S.E. of three independent experiments.

The effects of NM-3 on DEX induced cell death in RPMI8662 and U266 cells are shown in FIG. 13. and FIG. 14 respectively (48 hour preincubation shown in panels A and 72 hour preincubation shown in panels B). NM-3 potentiated DEX-induced cell death. NM-3 pretreatment alone resulted in a dose dependent decrease in cell viability after the 48 hour preincubation. However, this decrease in cell viability was less evident after 72 hours preincubation at concentrations of 50 and 100 µg/ml NM-3. Addition of DEX alone had a significant effect on cell viability after a 48 hour preincubation but did not result in a decrease in cell viability after 72 hours preincubation. Addition of NM-3 resulted in greater cell death than observed with DEX alone, this effect being most evident after 72 hour preincubation with 100 µg/ml NM-3 with both cell lines, wherein neither NM-3 nor DEX had a substantial effect alone while the combination of NM-3 and DEX had a pronounced effect on cell viability.

REFERENCES

Alexanian et al., "Primary dexamethasone treatment of multiple myeloma," Blood, 80:887–890, 1992.

Anderson et al., "Multiple Myeloma: new insights and therapeutic approaches," Hematology (Am. Soc. Hematol. Educ. Program) 2000, 147–165, 2000.

Barlogie et al., "Effective treatment of advanced multiple myeloma refractory to alkylating agents," N. Eng. J. Med., 310:1353–1356, 1984.

Bergsagel, "Chemotherapy of myeloma," in Myeloma: Biology and Management (Malpas et al., eds, 2d Ed.) Oxford University Press, Oxford, England, 269–302, 1998.

Bringmann et al., J. Organomet. Chem., 472:275–284, 1994.

Bringmann et al., Z. Naturforsch. B 52:355–358, 1997.

Case et al., "Improved survival times in multiple myeloma treated with melphan, prednisone, cyclophosphamide, vincristine and BCNU: M-2 protocol," Am. J. med., 63:897–903, 1977.

Couture et al., "A new and concise synthesis of 3-aryl- and 3-alkyl-1H-2-benzothiopyran-ones (thioisocoumarin)," Synthesis 12:1133–4, 1990.

Cloeman, "Glucocorticoids in cancer therapy," Biotherapy, 4:37–44, 1992.

Dijksman & Newbold, J. Chem. Soc., 1213, 1216, 1951.

Fidler, "Macrophages and metastasis—a biological approach to cancer therapy," Cancer Res., 45:4714–26, 1985.

Fidler & Baker, "The biology of cancer metastasis and implications for therapy," Curr. Probl. Surg., 24:129–209, 1987.

Fidler & Poste, "The cellular heterogeneity of malignant neoplasms: Implications for adjuvant chemotherapy," Semin. Oncol., 12:207–21, 1985.

Folkman., "Tumor angiogenesis: therapeutic implications," N. Engl. J. med., 285:1182–16, 1971.

Folkman, "How is blood vessel growth regulated in normal and neoplastic tissue?" Cancer Res. 46:467–73, 1986.

Folkman, "Successful treatment of an angiogenic disease," N. Engl. J. Med., 320:1211–12, 1989.

Gaynon & Lustig, "The use of glucocorticoids in acute lymphoblastic leukemia of childhood: Molecular, cellular, and clinical considerations," J. Pediatr. Hematol. Oncol. 17:1–12, 1995.

Geley et al., "Resistance to glucocorticoid-induced apoptosis in human T-cell acute leukemia CEM-C1 cells is due to insufficient glucocorticoid receptor expression," Cancer Res., 56:5033–5038, 1996.

Gahrton & Durie, Multiple Myeloma, Oxford University Press, New York, 1996

Gregory et al., "Combination chemotherapy versus melphalan and prednisolone in the treatment of multiple myeloma: overview of published trials," J. Clin. Oncol., 10:334–42, 1992.

Hata & Atsushi, Chem. Lett., 309–312, 1983.

Holmgren et al., "Dormancy of micrometastases: balanced proliferation and apoptosis in the presence of angiogenesis suppression," Nat. Med., 1:149–53, 1995.

Kennedy et al., "Vinyl azides in heterocyclic synthesis. Part 9. Synthesis of the isoquinolone alkaloid siamine by intramolecular aza-wittig reaction," J. Chem. Soc., Perkin Trans. 6:1395–8, 1987.

Kiang & Mann, J. Chem. Soc., 1909, 1914, 1951.

Letcher et al., J. Chem. Soc. Perk. Trans., 1(10): 1715–1720, 1998.

Myeloma Trialists' Collaborative Group, "Combination chemotherapy versus melphalan plus prednisone as treatment for multiple myeloma: an overview of 6,633 patients from 27 randomized trials." J. Clin. Oncol., 16:3823–42, 1998.

Norisuke, Bull. Chem. Soc. Japan, 58:1088–1093, 1985.

O'Reilly et al., "Angiostatin: a novel angiogenesis inhibitor that mediates the suppression of metastasis by a Lewis lung carcinoma," Cell, 79:315–28, 1994.

O'Reilly et al., "Angiostatin induces and sustains dormancy of human primary tumors in mice," Nat. Med., 2:689–92, 1996.

Padwa et al., J. Org. Chem., 64:3595–3607, 1999.

Pirotte et al., "Glucocorticoid-induced longterm remission in primary cerebral lymphoma: case report and review of the literature," J. Neurooncol., 32:63–69, 1997.

Planey & Litwack, "Glucocorticoid-induced apoptosis in lymphocytes," Biochem. Biphys. Res. Commun., 279:307–312, 2000

Ramdas et al., "Glucocorticoid-induced cell death requires autoinduction of glucocorticoid receptor expression in human leukemic T cells," Cancer Res., 59:1378–1385, 1999)

Sakamoto et al., Chem. Pharm. Bull. 33:626–633, 1985.

Segeren et al., "Vincristine, doxorubcin and dexamethasone (VAD) administration as rapid intravenous infusion for first-line treatment in untreated multiple myeloma," Brit. J. Heamatol., 105:127–130, 1999.

Singh et al., Synthesis, 10:791–793, 1983.

Spassov et al, Magn. Res. Chem., 23:795–799, 1985.

Sugarbaker et al., "Some characteristics of metastasis in man," Am. J. Pathol., 97:623–32, 1979.

Tonko et al., "Gene expression profiles of proliferating vs. G1/G0 arrested human leukemia cells suggest a mechanism for glucocorticoid-induced apoptosis," FASEB J., 15:693–99, 2001.

Weidner, "Tumor angiogenesis: review of current applications in tumor prognostication," Semin. Diagn. Pathol., 10:302–13, 1993.

Wiedner et al., "Tumor angiogenesis and metastasis—correlation in invasive breast carcinoma.," N. Engl. J. Med., 324:1–8, 1991.

Woodroofe et al., J. Chem. Soc. Perk. Trans., 2(1): 55–60 (2000).

Yousif et al., Chem. Pharm. Bull., 30:1680–1691, 1982.

What is claimed is:

1. A method for inducing cell death in a myeloma cancer cell, comprising contacting said myeloma cancer cell with an isocoumarin derivative of the formula:

[Structure: isocoumarin derivative with CH3O, OH, CH3, COOH substituents]

and further contacting said myeloma cancer cell with a glucocorticoid, wherein the dose of said isocoumarin derivative when combined with the dose of said glucocorticoid is effective to induce cell death in said myeloma cancer cell.

2. The method of claim 1, wherein said inducing cell death comprises inducing apoptosis.

3. The method of claim 2, wherein said glucocorticoid is dexamethasone or prednisone.

4. The method of claim 1, further comprising contacting said myeloma cancer cell with one or more other chemotherapeutic agents.

5. The method of claim 4, wherein said one or more other chemotherapeutic agents is or are selected from the group consisting of vincristine, doxorubicin, cyclophosphamide, etopside, cisplatin, melphalan, mitoxantrone, BCNU, idarubicin, procarbazine, and cytoxan.

6. A method for inhibiting the proliferation of a myeloma cancer cell, comprising contacting said myeloma cancer with an isocoumarin derivative of the formula:

[Structure: isocoumarin derivative with CH3O, OH, CH3, COOH substituents]

and further contacting said myeloma cancer cell with a glucocorticoid, wherein the dose of said isocoumarin derivative when combined with the dose of said glucocorticoid is effective to inhibit the proliferation of said myeloma cancer cell.

7. The method of claim 6, wherein said glucocorticoid is dexamethasone or prednisone.

8. The method of claim 6, further comprising contacting said myeloma cancer cell with one or more other chemotherapeutic agents.

9. The method of claim 8, wherein said one or more other chemotherapeutic agents is or are selected from the group consisting of vincristine, doxorubicin, cyclophosphamide, etopside, cisplatin, melphalan, mitoxantrone, BCNU, idarubicin, procarbazine, and cytoxan.

10. A method for treating multiple myeloma in a human patient, comprising administering an isocoumarin derivative of the formula:

[Structure: isocoumarin derivative with CH3O, OH, CH3, COOH substituents]

and administering a glucocorticoid as a second treatment modality, wherein the administration of said isocoumarin derivative when combined with the administration of said glucocorticoid, is effective to treat said multiple myeloma.

11. The method of claim 10, wherein said glucocorticoid is dexamethasone or prednisone.

12. A method for treating multiple myeloma in a human patient, comprising administering an isocoumarin derivative of the formula:

[Structure: isocoumarin derivative with CH3O, OH, CH3, COOH substituents]

and administering a glucocorticoid as a second treatment modality and administering one or more other chemotherapeutic agents as further treatment modalities, wherein the administration of said isocoumarin derivative when combined with the administration said glucocorticoid and administration of said one or more other chemotherapeutic agents is effective to treat said multiple myecloma.

13. The method of claim 12, wherein said glucocorticoid is dexamethasone.

14. The method of claim 13, wherein said administration of one or more other chemotherapeutic agents is the administration of vincristine as a third treatment modality and the administration of doxorubicin as a fourth treatment modality.

15. The method of claim 12, wherein said one or more other chemotherapeutic agents is or are selected from the group consisting of vincristine, doxorubicin, cyclophosphamide, etopside, cisplatin, melphalan, BCNU and idarubicin.

16. The method of claim 12, wherein said glucocorticoid is prednisone.

17. The method of claim 16, wherein said administration of one or more other chemotherapeutic agents is:

(a) the administration of melphalan as a third treatment modality;

(b) the administration of cyclophosphamide as a third treatment modality; or (c) the administration of vincristine as a third treatment modality, BCNU as a fourth treatment modality, melphalan as a fifth treatment modality and cyclophosphamide as a sixth treatment modality.

18. The method of claim 16, wherein said one or more chemotherapeutic agents is or are selected from the group consisting of melphalan, mitoxantrone, cyclophosphamide, vincristine, procarbazine, cytoxan, BCNU and doxorubicin.

* * * * *

UNITED STATES PATENT AND TRADEMARK OFFICE
CERTIFICATE OF CORRECTION

PATENT NO. : 6,900,239 B2
DATED : May 31, 2005
INVENTOR(S) : Agata et al.

It is certified that error appears in the above-identified patent and that said Letters Patent is hereby corrected as shown below:

<u>Title page,</u>
Item [73], Assignee, please delete "ILWZ".

Signed and Sealed this

Twenty-second Day of November, 2005

JON W. DUDAS
*Director of the United States Patent and Trademark Office*